(12) United States Patent
Ebi et al.

(10) Patent No.: US 8,906,674 B2
(45) Date of Patent: Dec. 9, 2014

(54) SAMPLE PREPARATION APPARATUS AND CELL ANALYZER

(75) Inventors: Ryuichiro Ebi, Osaka (JP); Koki Tajima, Kobe (JP)

(73) Assignee: Sysmex Corporation, Hyogo (JP)

(*) Notice: Subject to any disclaimer, the term of this patent is extended or adjusted under 35 U.S.C. 154(b) by 919 days.

(21) Appl. No.: 12/893,806

(22) Filed: Sep. 29, 2010

(65) Prior Publication Data

US 2011/0076755 A1 Mar. 31, 2011

(30) Foreign Application Priority Data

Sep. 30, 2009 (JP) ................. 2009-227761
Aug. 23, 2010 (JP) ................. 2010-186434

(51) Int. Cl.
| | | |
|---|---|---|
| C12M 1/12 | (2006.01) |
| B01D 35/00 | (2006.01) |
| G01N 1/34 | (2006.01) |
| G01N 1/40 | (2006.01) |
| B01F 13/08 | (2006.01) |
| B01L 3/00 | (2006.01) |
| G01N 1/38 | (2006.01) |
| B01L 3/02 | (2006.01) |
| B01L 7/00 | (2006.01) |

(52) U.S. Cl.
CPC .............. *G01N 1/40* (2013.01); *B01F 13/0818* (2013.01); *B01L 3/502* (2013.01); *G01N 1/38* (2013.01); *B01L 3/021* (2013.01); *B01L 3/52* (2013.01); *B01L 7/00* (2013.01); *B01L 2200/0647* (2013.01); *B01L 2200/14* (2013.01); *B01L 2200/143* (2013.01); *B01L 2300/0681* (2013.01); *B01L 2300/0832* (2013.01); *B01L 2300/0858* (2013.01); *G01N 2001/4088* (2013.01)
USPC ............. 435/308.1; 435/286.5; 435/287.3; 435/297.2; 422/534; 422/559

(58) Field of Classification Search
USPC .............. 435/297.2, 308.1; 422/534, 536
See application file for complete search history.

(56) References Cited

U.S. PATENT DOCUMENTS

| | | | | |
|---|---|---|---|---|
| 4,043,903 A | * | 8/1977 | Dor ................................ 47/1.4 |
| 2007/0278154 A1 | * | 12/2007 | Nagaoka et al. ............. 210/644 |
| 2008/0108103 A1 | | 5/2008 | Ishisaka et al. | |

FOREIGN PATENT DOCUMENTS

| | | |
|---|---|---|
| JP | 2010-172251 A | 8/2010 |
| WO | 2006/103920 A1 | 10/2006 |

* cited by examiner

*Primary Examiner* — William H Beisner
(74) *Attorney, Agent, or Firm* — Sughrue Mion, PLLC

(57) ABSTRACT

A sample preparation apparatus comprising: a storage chamber that can store therein a liquid sample including an analysis target to be analyzed; a concentrated sample storage chamber that is provided to communicate with the storage chamber and that stores therein concentrated liquid having an analysis target having a higher concentration than that of the liquid sample; and an analysis target transportation section for transporting the analysis target included in the liquid sample stored in the storage chamber to the concentrated sample storage chamber. A cell analyzer is also disclosed.

18 Claims, 23 Drawing Sheets

SAMPLE PREPARATION APPARATUS AND CELL ANALYZER

FIELD OF THE INVENTION

The present invention relates to a sample preparation apparatus and a cell analyzer.

BACKGROUND

Conventionally, as a cell analyzer for analyzing cells included in a living body sample extracted from a living body, there has been known a cell analyzer in which epidermal cells of a cervix included in a sample extracted from the cervix of a subject are measured by a flow cytometer to perform the screening of cancer cells and atypical cells (e.g., see Pamphlet of international publication No. 2006/103920).

In the cell analyzer as described above, the individual cells are analyzed with regard to whether the cells are a normal cell or a cancer or an atypical cell. Thus, in order to improve the measurement accuracy, the number of cells to be analyzed is preferably higher.

An increased amount of sample to be measured can increase the number of to-be-measured cells but requires a longer time for the measurement to thereby cause disadvantages of a lower analysis speed and an increased consumption amount of reagent. To solve this, there has been required a technique to increase the concentration of cells included in a measurement sample.

SUMMARY OF INVENTION

The scope of the present invention is defined solely by the appended claims, and is not affected to any degree by the statements within this summary.

A first aspect of the present invention is a sample preparation apparatus, comprising: a storage chamber that can store therein a liquid sample including an analysis target to be analyzed; a concentrated sample storage chamber that is provided to communicate with the storage chamber and that stores therein concentrated liquid having an analysis target having a higher concentration than that of the liquid sample; and an analysis target transportation section for transporting the analysis target included in the liquid sample stored in the storage chamber to the concentrated sample storage chamber.

A second aspect of the present invention is a sample preparation apparatus comprising: a storage chamber that can store therein a liquid sample including an analysis target to be analyzed; a concentrated sample storage chamber that is provided to communicate with the storage chamber and that stores therein concentrated liquid having an analysis target having a higher concentration than that of the liquid sample; an analysis target transportation section for transporting the analysis target included in the liquid sample stored in the storage chamber to the concentrated sample storage chamber; a container capable of storing a liquid sample including an analysis target to be analyzed; and a cylindrical body capable of moving in the container in a up-and down direction, wherein the storage chamber and the concentrated sample storage chamber are provided at a bottom portion of the container, and the filter is provided at a lower end face of the cylindrical body, and wherein the liquid is designed to be separated into a first liquid including the analysis target to be analyzed and a second liquid including a non-analysis target having a smaller diameter than that of the analysis target.

A third aspect of the present invention is a cell analyzer comprising: a storage chamber that can store therein a liquid sample including an analysis target to be analyzed; a concentrated sample storage chamber that is provided to communicate with the storage chamber and that stores therein concentrated liquid having an analysis target having a higher concentration than that of the liquid sample; an analysis target transportation section for transporting the analysis target included in the liquid sample stored in the storage chamber to the concentrated sample storage chamber; a liquid acquisition section for acquiring the liquid sample including the cell stored in the concentrated sample storage chamber; and an analysis section for analyzing a cell included in the liquid sample acquired by the liquid acquisition section.

DESCRIPTION OF EMBODIMENTS

Hereinafter, with reference to the attached drawings, the following section will describe in detail an embodiment of the sample preparation apparatus and the cell analyzer of the present invention.

First Embodiment

Entire Configuration of Cell Analyzer

Figure 1:
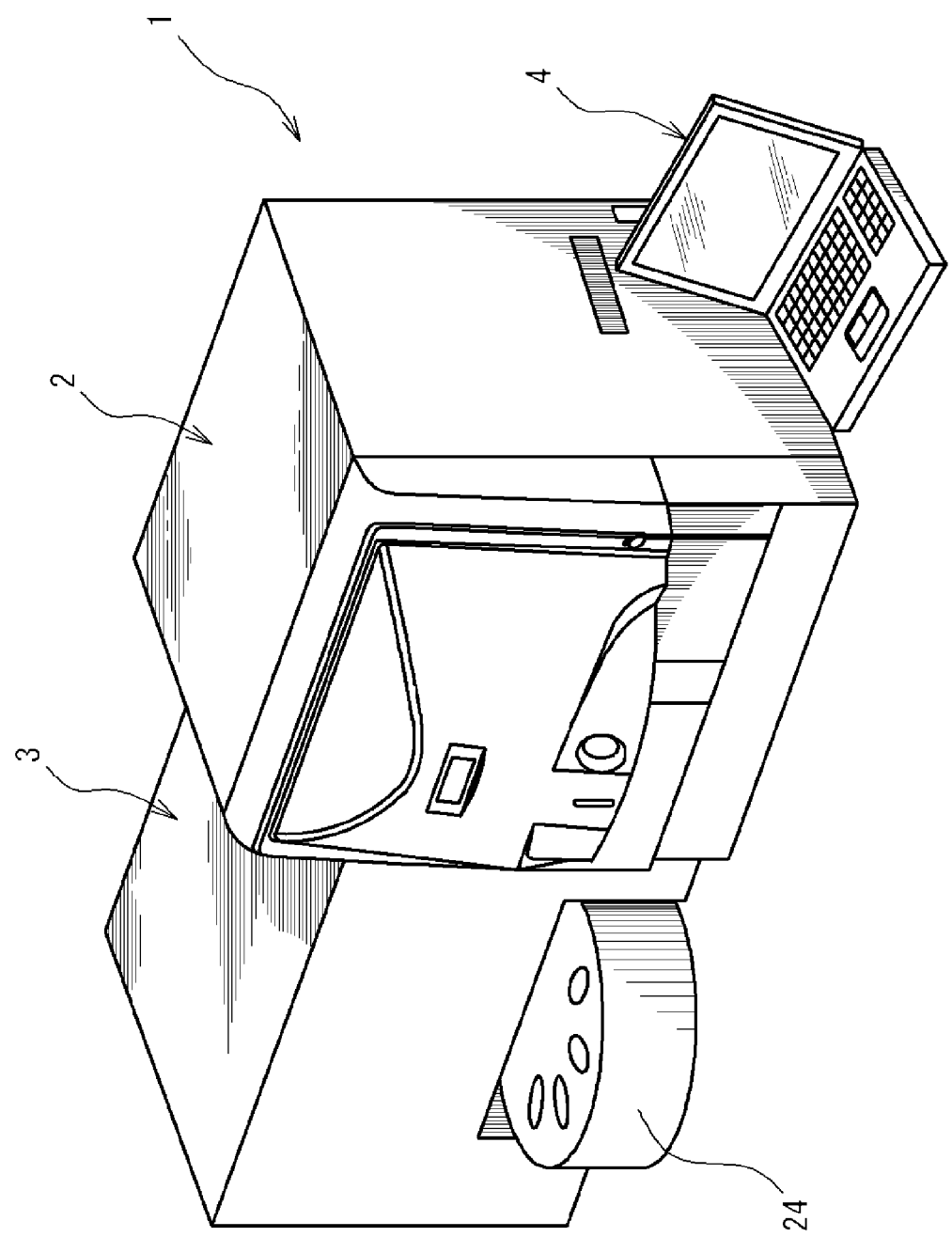
FIG. 1 is a perspective view illustrating a cell analyzer according to the first embodiment.

FIG. 1 is a perspective view illustrating a cell analyzer 1 according to an embodiment (first embodiment) of the present invention.

This cell analyzer 1 causes a measurement sample including cells extracted from a patient to flow in a flow cell, emits laser beam to the measurement sample flowing in the flow cell, detects the light from the measurement sample (e.g., forward scattered light, side fluorescence) to analyze the optical signal to thereby determine whether the cells include a cancer cell or not.

More specifically, the cell analyzer 1 of the present embodiment is used to analyze epidermal cells of a cervix and is used to screen a cervical cancer.

As shown in FIG. 1, the cell analyzer 1 comprises: a measurement apparatus 2 for subjecting a measurement sample to an optical measurement by laser beam; a sample preparation apparatus 3 for subjecting a living body sample extracted from a subject to a preprocessing (e.g., cleaning or staining) to prepare a measurement sample to be supplied to the measurement apparatus 2; and a data processing apparatus 4 for analyzing the measurement result by the measurement apparatus 2 for example.

The following section will sequentially describe main constituent elements of a cell analyzer 1.

[Internal Configuration of Measurement Apparatus]

Figure 2:
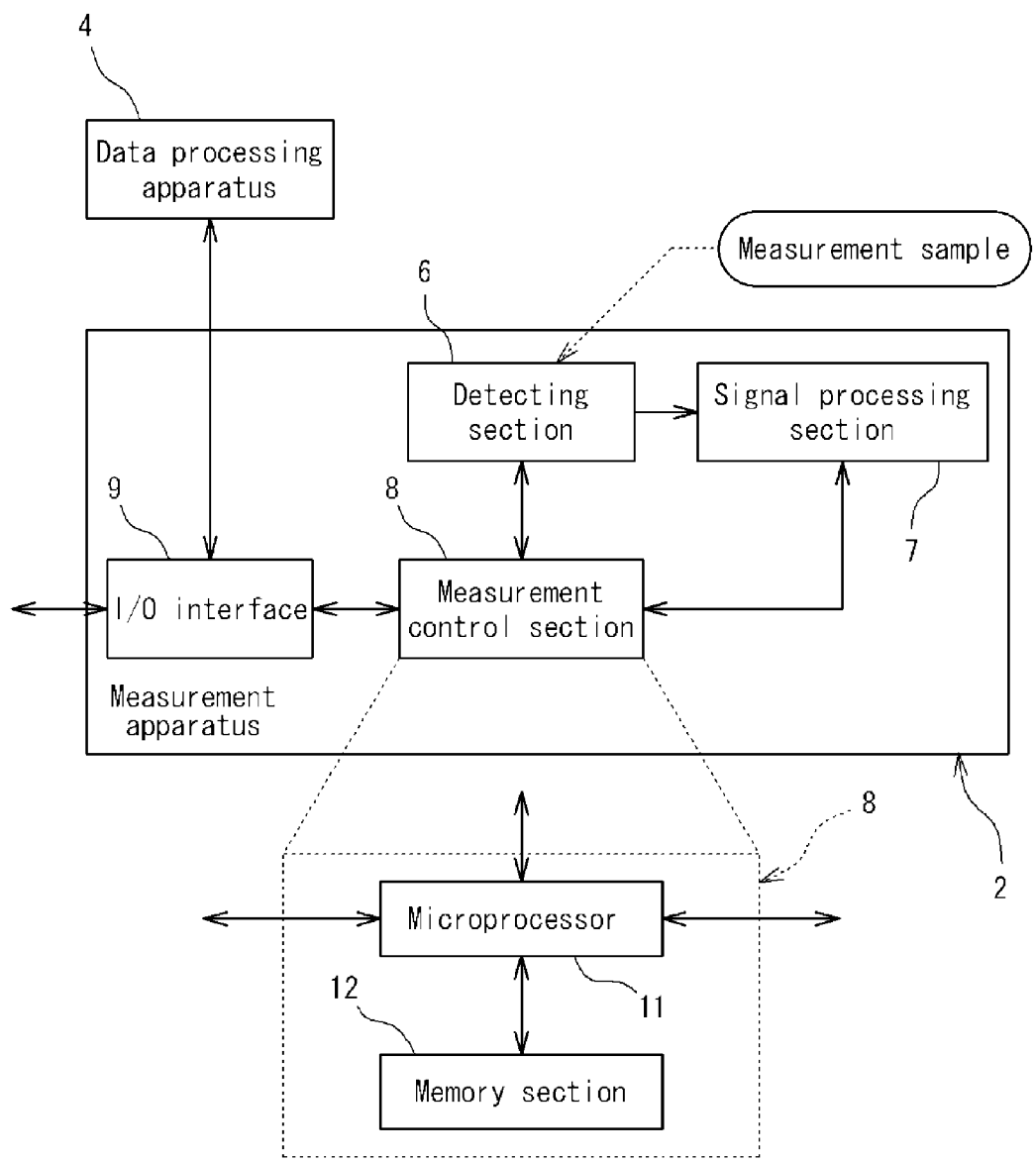
FIG. 2 is a block diagram illustrating the internal configuration of a measurement apparatus.

FIG. 2 is a block diagram illustrating the internal configuration of the measurement apparatus 2.

As shown in FIG. 2, this measurement apparatus 2 comprises: a detection section 6; a signal processing section 7; a measurement control section 8; and an I/O interface 9.

Figure 5:
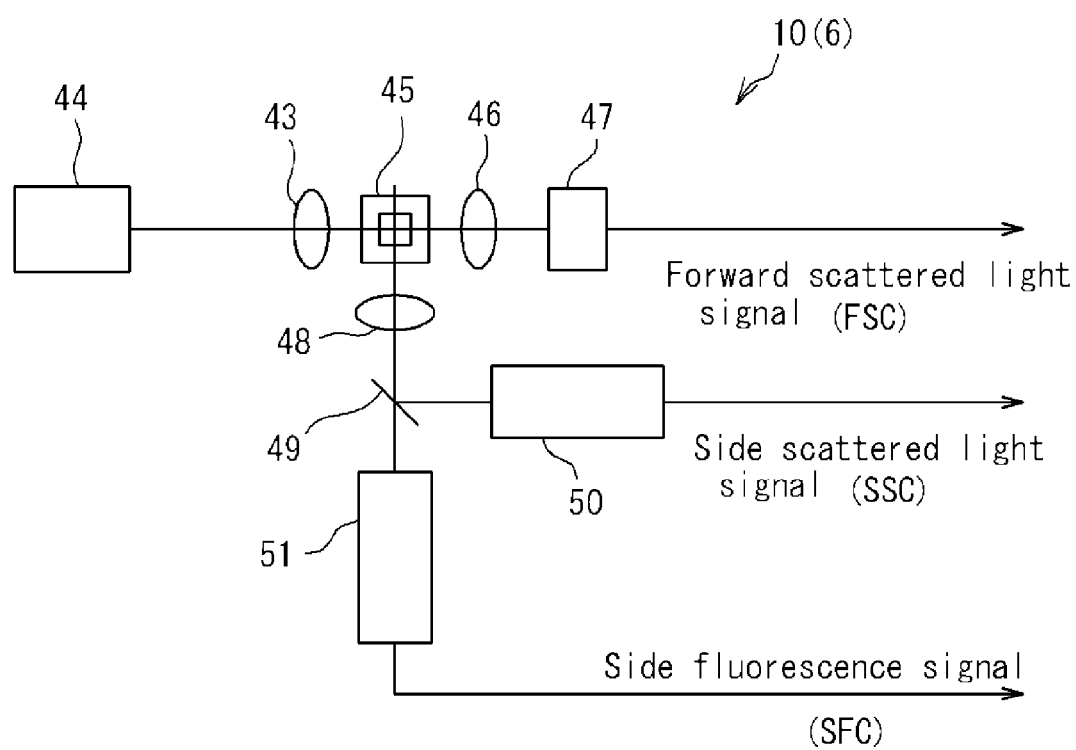
FIG. 5 is a function block diagram illustrating a flow cytometer configuring a detection section.
Figure 6:
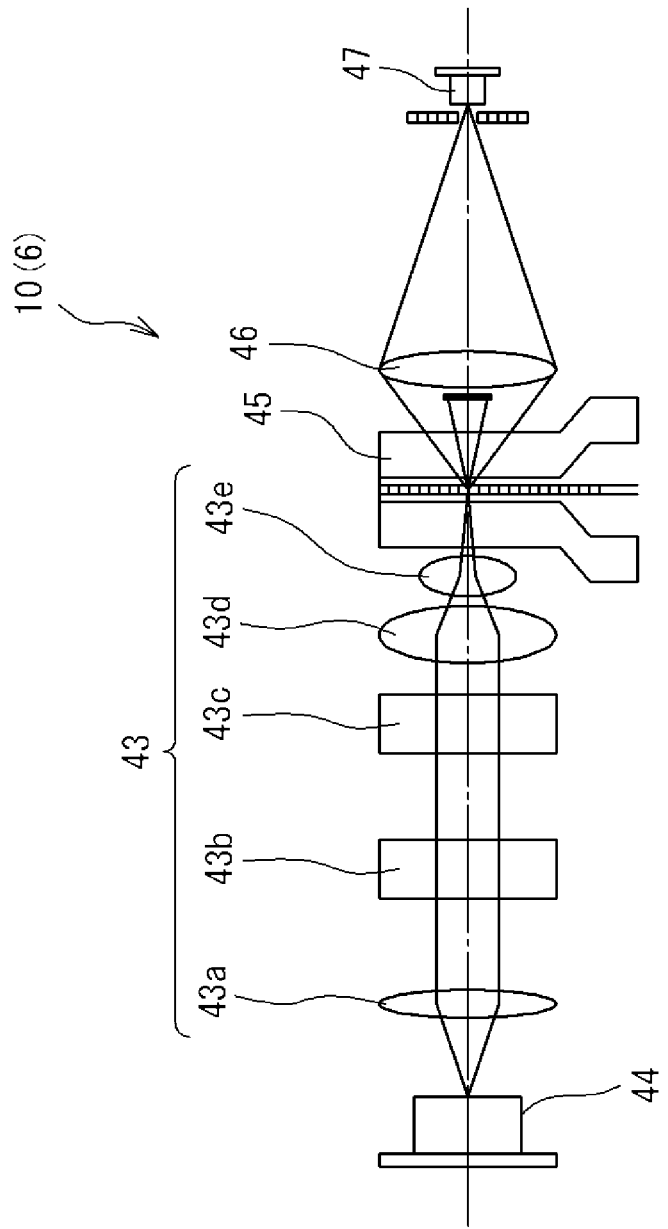
FIG. 6 is a side view illustrating an optical system of the flow cytometer.

Among these components, the detection section 6 detects, from a measurement sample, the number and size of a to-be-measured cell as well as nucleus thereof for example. In the present embodiment, a flow cytometer 10 shown in FIG. 5 and FIG. 6 is used.

The signal processing section 7 is composed of a signal processing circuit that performs a signal processing required for an output signal from the detection section 6. The measurement control section 8 includes a microprocessor 11 and a memory section 12. The memory section 12 is composed of ROM and RAM for example.

The memory section 12 includes a ROM that stores therein control programs for controlling the operations of the detection section 6 and the signal processing section 7 and data required to execute the control programs. The microprocessor 11 can load the control programs to a RAM or can execute the programs directly from the ROM.

The microprocessor 11 of the measurement control section 8 is connected, via the I/O interface 9, to the data processing apparatus 4 and a microprocessor 19 of a preparation control section 16 which will be described later. Thus, the data processed by the microprocessor 11 and the data required for the processing by the microprocessor 11 can be sent and received between the data processing apparatus 4 and the microprocessor 19 of the preparation control section 16.

[Internal Configuration of Sample Preparation Apparatus]

Figure 3:
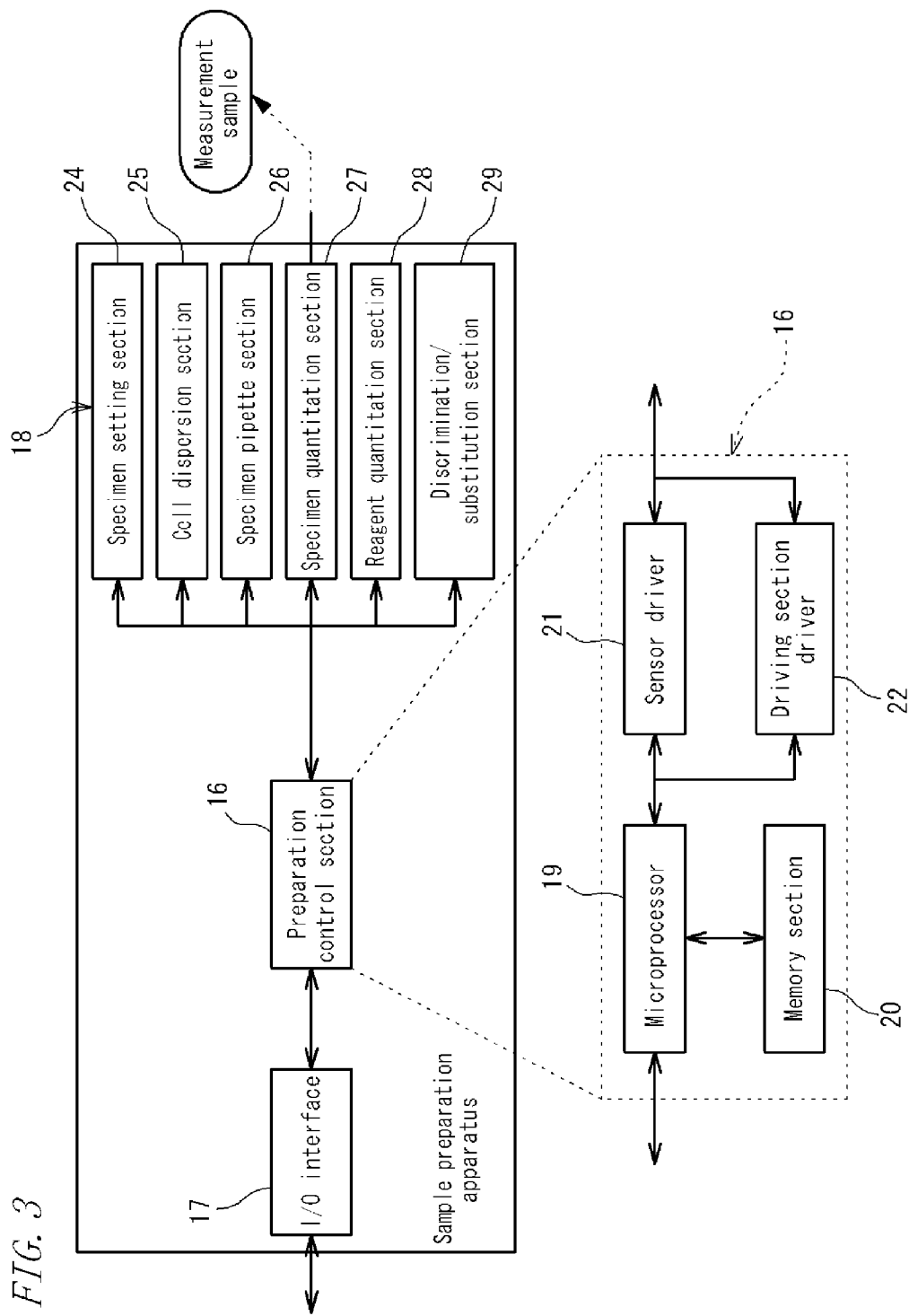
FIG. 3 is a block diagram illustrating the internal configuration of a sample preparation apparatus.

FIG. 3 is a block diagram illustrating the internal configuration of the sample preparation apparatus 3 according to the first embodiment.

As shown in FIG. 3, this sample preparation apparatus 3 comprises: the preparation control section 16; an I/O interface 17; and a preparation device section 18 for automatically subjecting a living body sample to a component adjustment.

The preparation control section 16 is composed of: the microprocessor 19; a memory section 20; a sensor driver 21; and a driving section driver 22. The memory section 20 is composed of ROM and RAM for example.

The preparation device section 18 of the present embodiment is composed of: a specimen setting section 24; a cell dispersion section 25; a specimen pipette section 26; a specimen quantitation section 27; a reagent quantitation section 28; and a discrimination/substitution section 29.

Among them, the specimen setting section 24 is used to set a plurality of living body containers 53 and measurement sample containers 54 (see FIG. 7) that store living body samples extracted from a patient and preservative solution containing methanol as a major components. The cell dispersion section 25 agitates mixed liquid of the living body sample and the preservative solution in the living body container 53 to forcedly disperse the cells included in the sample.

The specimen pipette section 26 is used to remove the mixed liquid of the living body sample and the preservative solution in which the cells are dispersed from the living body container 53 to introduce the liquid to the fluid circuit of the preparation device section 18 or is used to return a prepared liquid sample to the measurement sample container 54 or to remove the liquid sample from the measurement sample container 54. The specimen quantitation section 27 quantifies the mixed liquid of the living body sample and the preservative solution supplied to the fluid circuit. The reagent quantitation section 28 quantifies a reagent such as a staining fluid added to a living body sample.

A discrimination/substitution section 29 substitutes preservative solution and diluting fluid and discriminates a to-be-measured cell from cells other than the to-be-measured cell (e.g., red blood cells, white blood cells) and bacteria for example. The discrimination/substitution section 29 is also used to obtain, from the liquid sample including the to-be-measured cell subjected to the discrimination and substitution, a liquid sample having the to-be-measured cell with an increased concentration. The configuration of the fluid circuit of the preparation device section 18 having the respective sections 24 to 29 (FIG. 7 to FIG. 8) will be described later.

The ROM of the memory section 20 stores therein the control programs used to control the operations of the sensor driver 21 and the driving section driver 22 and the data required to execute the control programs. The control program can be loaded by the microprocessor 19 to the RAM for execution or can be directly executed from the ROM.

The microprocessor 19 of the preparation control section 16 is connected, via the I/O interface 17, to the microprocessor 11 of the measurement control section 8. Thus, the data processed by the microprocessor 19 and the data required for the processing by the microprocessor 19 can be sent and received between the microprocessor 19 and the microprocessor 11 of the measurement processing section 8.

The microprocessor 19 of the preparation control section 16 is connected, via the sensor driver 21 and the driving section driver 22, to the sensors or the like of the respective sections 24 to 29 of the preparation device section 18 and a driving motor configuring a driving section. Based on a sensing signal from a sensor, the microprocessor 19 executes a control program to control the operation of the driving section.

[Internal Configuration of Data Processing Section]

Figure 4:
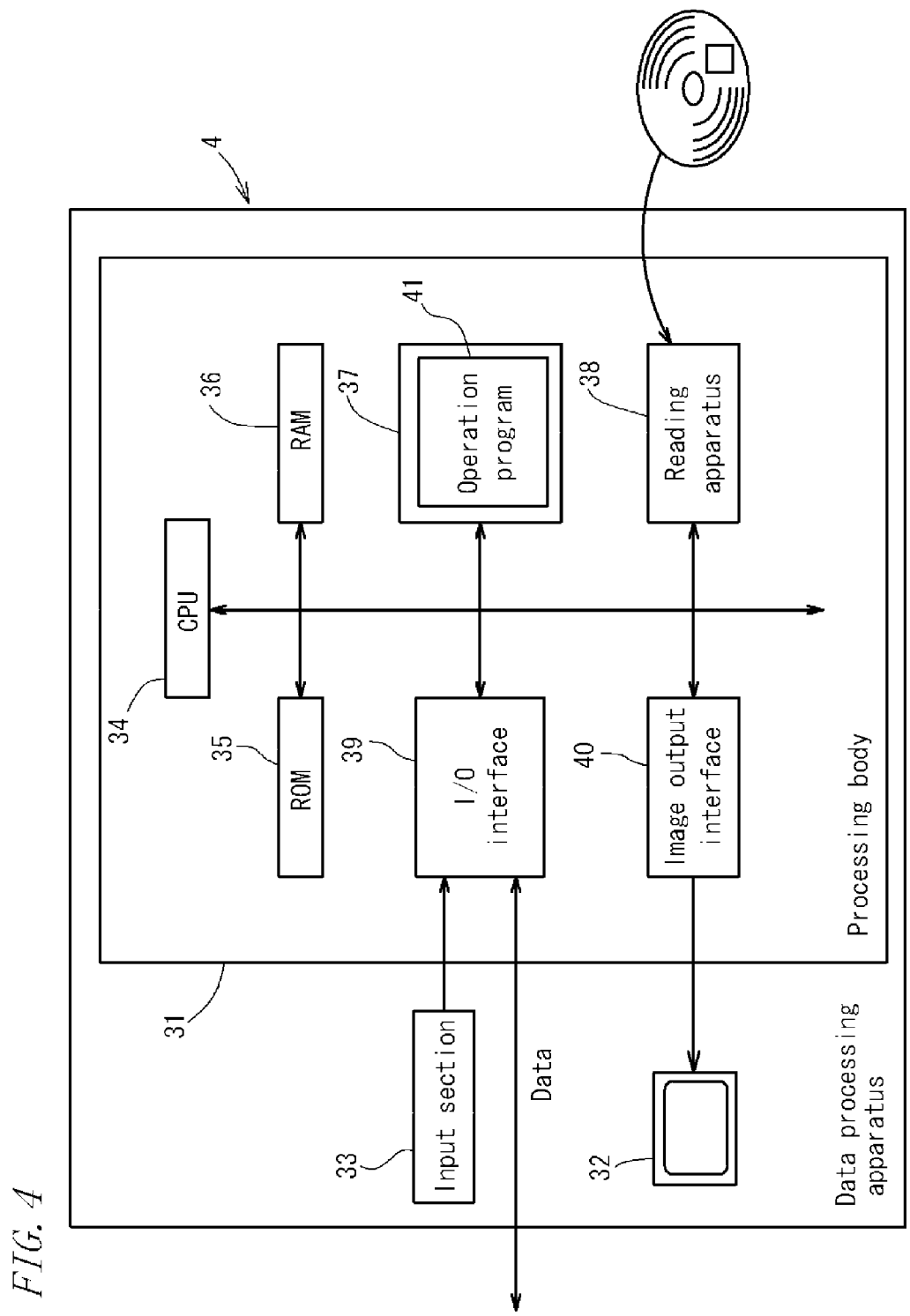
FIG. 4 is a block diagram illustrating the internal configuration of a data processing apparatus.

FIG. 4 is a block diagram illustrating the internal configuration of the data processing apparatus 4.

As shown in FIG. 4, the data processing apparatus 4 of the present embodiment comprises, for example a personal computer such as a laptop PC (or a desk top PC) and is mainly composed of a processing body 31, a display section 32, and an input section 33.

The processing body 31 comprises: a CPU 34; a ROM 35; a RAM 36; a hard disk 37; a reading apparatus 38; an input/output interface 39; and an image output interface 40. The respective sections are connected via an internal bus so that these sections can communicate to one another.

The CPU 34 can execute a computer program memorized in the ROM 35 and a computer program loaded to the RAM 36.

The ROM 35 is configured by a mask ROM, PROM, EPROM, EEPROM or the like and stores therein a computer program executed by the CPU 34 and the data used for the computer program for example.

The RAM 36 is configured by SRAM or DRAM for example. The RAM 36 is used to read various computer programs recorded in the ROM 35 and the hard disk 37 and is used as a working region of the CPU 34 to execute these computer programs.

In the hard disk 37, various computer programs to be executed by the CPU 34 such as an operating system and an application program and the data used to execute the programs are installed.

In the hard disk 37, there is installed an operating system that provides, for example, a graphical user interface environment such as Windows® manufactured and sold by U.S. Microsoft Corporation.

Furthermore, in the hard disk 37, an operation program 41 is installed for the transmission of an operation instruction to the measurement control section 8 and the preparation control section 16, for the reception and analysis processings of the measurement result performed by the measurement apparatus 2, and for the display of the processed analysis result. This operation program 41 operates on the operating system.

The reading apparatus 38 is configured by a flexible disk drive, a CD-ROM drive, or a DVD-ROM drive and can read a computer program or data recorded in a mobile recording medium.

The input/output interface 39 is composed of, for example, a serial interface such as USB, IEEE1394, or RS-232C, a parallel interface such as SCSI, IDE, or IEEE1284, and an analog interface such as a D/A converter or an A/D converter.

The input/output interface 39 is connected to the input section 33 composed of a keyboard and a mouse. By allowing a user to operate the input section 33, data can be inputted to the computer.

The input/output interface 39 is also connected to the I/O interface 9 of the measurement apparatus 2 to thereby provide data transmission and reception between the measurement apparatus 2 and the data processing apparatus 4.

The image output interface 40 is connected to the display section 32 composed of LCD or CRT. The image output interface 40 causes the display section 32 to output a video signal depending on the image data from the CPU 34.

[Configuration of Detection Section (Flow Cytometer)]

FIG. 5 is a function block diagram of the flow cytometer 10 configuring the detection section 6. FIG. 6 is a side view illustrating the optical system of the flow cytometer 10.

As shown in FIG. 5, the flow cytometer 10 has a lens system 43 that collects the laser beam from a semiconductor laser 44 as a light source to a measurement sample flowing in a flow cell 45. A collecting lens 46 collects the forward scattered light from cells in the measurement sample to a scattered light detector composed of a photodiode 47.

Although FIG. 5 shows the lens system 43 by a single lens, the lens system 43 actually has a configuration as shown in FIG. 6 for example.

In other words, the lens system 43 of the present embodiment is composed of, in an order from the semiconductor laser 44 (left side of FIG. 6), a collimator lens 43a, a cylinder lens system (a planoconvex cylinder lens 43b+a biconcave cylinder lens 43c) and a condenser lens system (a condenser lens 43d+a condenser lens 43e).

Returning to FIG. 5, a side collecting lens 48 collects the side scattered light and the side fluorescence in the to-be-measured cell or the nucleus in the cell to a dichroic mirror 49. The dichroic mirror 49 reflects the side scattered light to the photomultiplier 50 as a scattered light detector and transmits the side fluorescence to a photomultiplier 51 as a fluorescence detector. These lights reflect the features of the cell in the measurement sample or the nucleus.

Then, the photodiode 47 as well as the respective photomultipliers 50 and 51 convert the received optical signal to an electric signal to output a forward scattered light signal (FSC), a side scattered light signal (SSC), and a side fluorescence signal (SFL), respectively. These output signals are amplified by a preamplifier (not shown) and is sent to the signal processing section 7 of the measurement apparatus 2 (FIG. 2).

The respective signals FSC, SSC, and SFL processed by the signal processing section 7 of the measurement apparatus 2 are sent by the microprocessor 11 from the I/O interface 9 to the data processing apparatus 4.

The CPU 34 of the data processing apparatus 4 executes the operation program 41 to thereby prepare a scattergram for analyzing the cell and nucleus based on the respective signals FSC, SSC, and SFL. Based on the scattergram, it is determined whether the cell in the measurement sample is abnormal or not, specifically, whether the cell is a cancerous cell or not.

It is noted that, although the flow cytometer 10 may have a light source composed of a gas laser instead of the semiconductor laser 44, the use of the semiconductor laser 44 is preferred from the viewpoints of low cost, small size, and low power consumption. The use of the semiconductor laser 44 as described above can reduce the product cost and can allow the apparatus to have a small size and power saving.

Furthermore, in the present embodiment, blue semiconductor laser having a short wavelength is used that is advantageously used to narrow beam. The blue semiconductor laser is also advantageous to a fluorescence excitation wavelength such as PI. It is noted that red semiconductor laser also may be used that is low-cost and long-life among semiconductor lasers and that can be supplied stably from manufacturers.

By the way, an epidermal cell of a cervix has an average size of about 60 μm and the nucleus has a size of 5 to 7 μm. When the cell becomes cancerous, the cell division frequency increases abnormally and the nucleus grows to a size of 10 to 15 μm. As a result, an N/C ratio (nucleus size/cell size) increases to a value larger than that of a normal cell.

Thus, by detecting the sizes of a cell and the nucleus, an indicator can be obtained that is used to determine whether the cell is cancerous or not.

Thus, in the present embodiment, the scattered light from a measurement sample flowing in the flow cell 45 is detected by the photodiode 47 and the fluorescence from the measurement sample flowing in the flow cell 45 is detected by the photomultiplier 51.

The signal processing section 7 of the measurement apparatus 2 acquires, from the scattered light signal outputted from the photodiode 47, a pulse width of the scattered light signal having a value reflecting the size of the to-be-measured cell and acquires, from the fluorescence signal outputted from the photomultiplier 51, a pulse width of the fluorescence signal having a value reflecting the size of the nucleus of the to-be-measured cell.

Then, based on the values obtained by the signal processing section 7 that reflect the size of the to-be-measured cell and the size of the nucleus of the to-be-measured cell, whether the to-be-measured cell is abnormal or not is determined by the CPU 34 of the data processing apparatus 4 configuring an analysis section.

Specifically, the CPU 34 of the data processing apparatus 4 determines that the to-be-measured cell is abnormal when a to-be-measured cell has a peak, a nucleolar size, or an area having a value higher than a predetermined threshold value.

[Fluid Circuit of Preparation Device Section]

Figure 7:
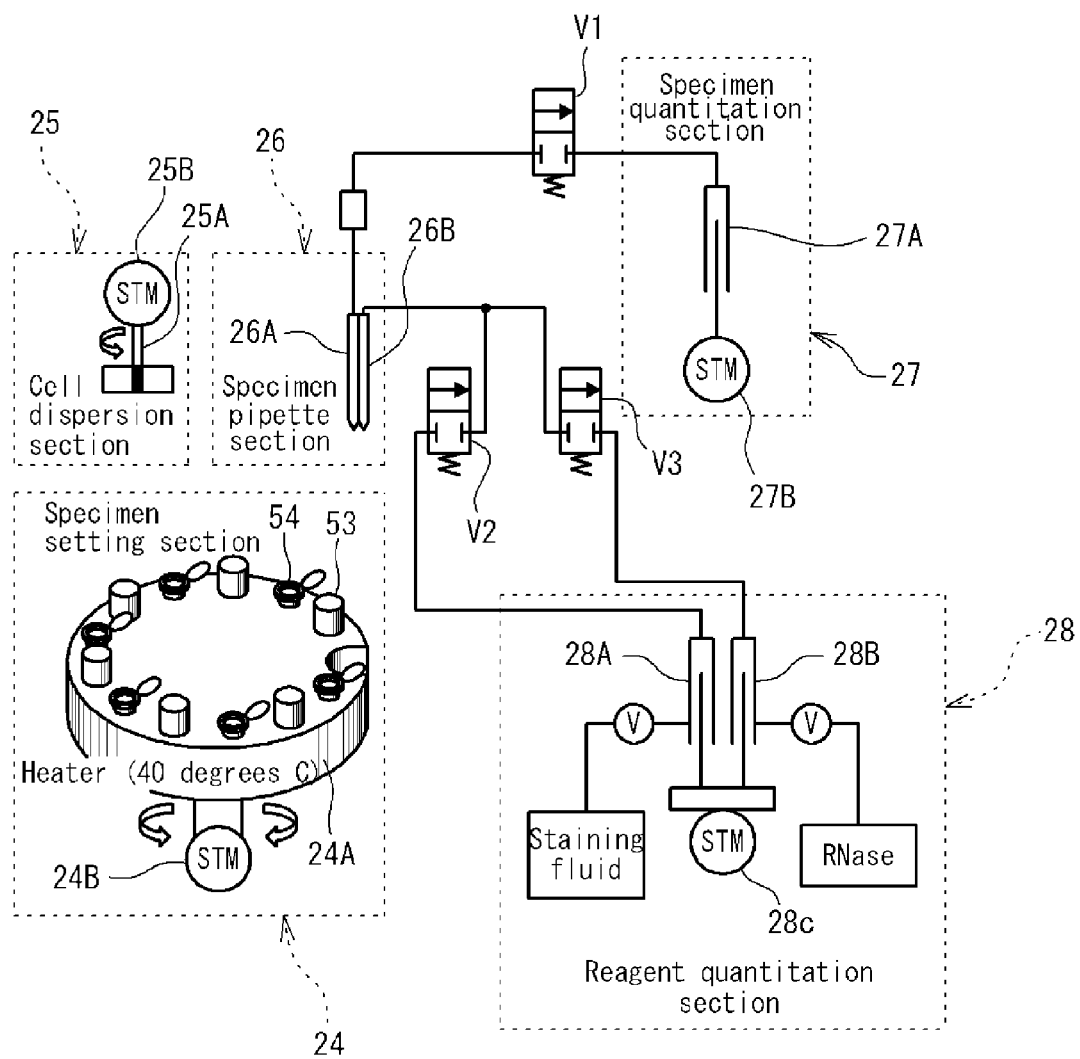
FIG. 7 is a fluid circuit diagram illustrating a preparation device section.
Figure 8:
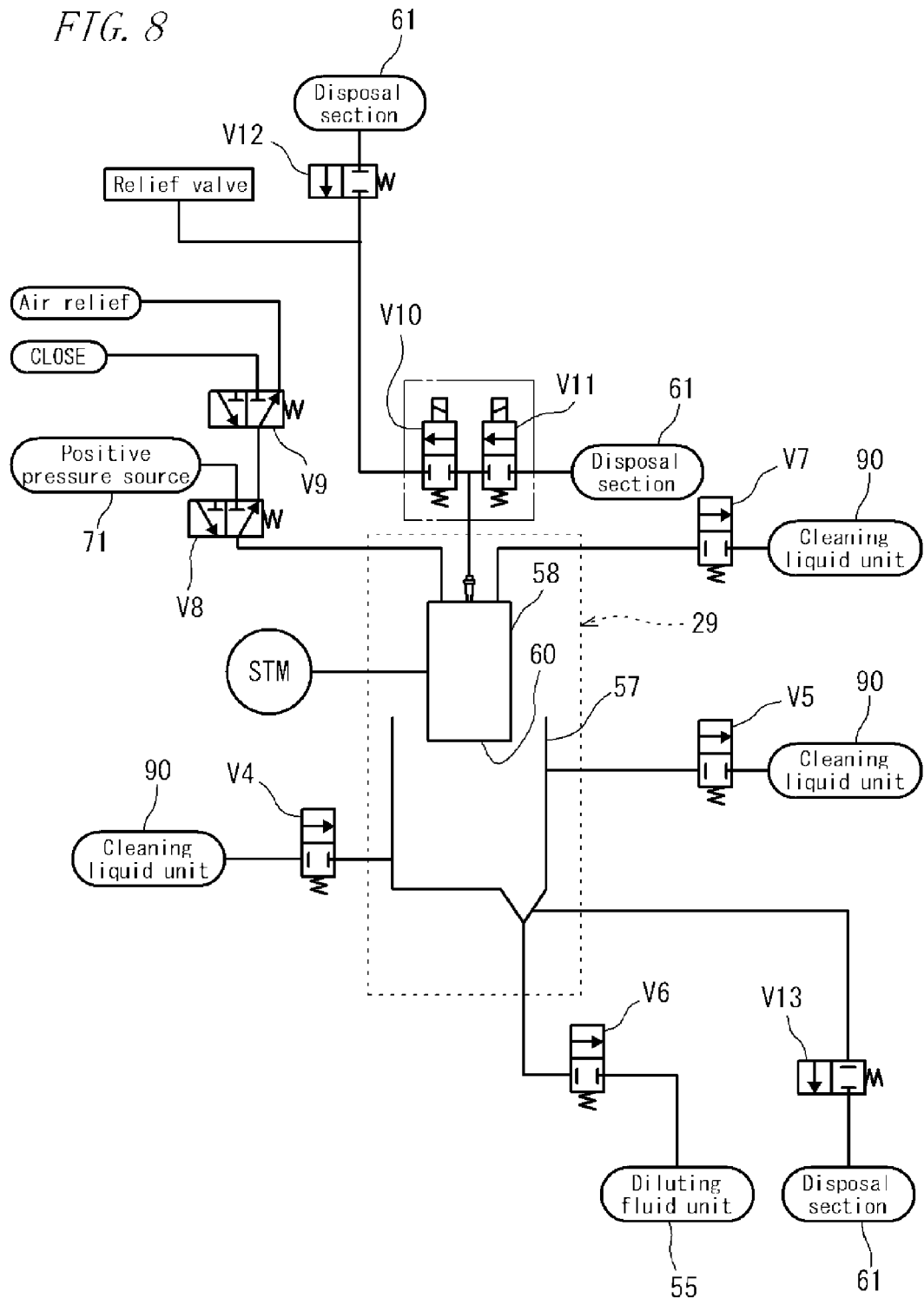
FIG. 8 is a fluid circuit diagram illustrating a preparation device section.

FIG. 7 illustrates a fluid circuit diagram of the preparation device section 18 comprising the specimen setting section 24, the cell dispersion section 25, the specimen pipette section 26, the specimen quantitation section 27, and the reagent quantitation section 28. FIG. 8 is a fluid circuit diagram of the discrimination/substitution section 29 of the preparation device section 18.

The specimen setting section 24 comprises a circular rotation table 24A and a driving section 24B for driving the rotation table 24A to rotate. The driving section 24B is composed of a stepping motor. At the outer circumference of the rotation table 24A, there is provided a retention section that can set the living body container 53 for storing mixed liquid of a living body sample and preservative solution and a measurement sample container (microtube) 54 for storing a liquid sample including a to-be-measured cell having an increased concentration that is prepared by the discrimination/substitution section 29.

The cell dispersion section 25 comprises an agitation bar 25A for agitating the mixed liquid of a living body sample and preservative solution in the living body container 53 and a driving section 25B for driving the agitation bar 25A to rotate. The driving section 25B is composed of a stepping motor that inserts the agitation bar 25A to the living body container 53 to rotate the agitation bar 25A. As a result, the mixed liquid in the living body container 53 can be agitated to thereby disperse the cells included in the living body sample.

The specimen pipette section 26 comprises: the first pipette 26A; and the second pipette 26B. The first pipette 26A sucks the mixed liquid of the living body sample and the preservative solution in the living body container 53, transports the mixed liquid to the substitution container 57 of the discrimination/substitution section 29, and discharges the mixed liquid into the substitution container 57. The mixed liquid discharged into the substitution container 57 is subjected to discrimination and substitution. Then, from the liquid sample including a to-be-measured cell subjected to discrimination and substitution, a liquid sample including the to-be-measured cell having an increased concentration is prepared. Thereafter, the first pipette 26A sucks from the substitution container 57 the liquid sample including the to-be-measured cell having an increased concentration, transports the liquid sample to the measurement sample container 54 placed in the specimen setting section 24, and discharges the liquid sample into the measurement sample container 54. The second pipette 26B discharges reagent such as staining fluid supplied from the reagent quantitation section 28 into the measurement sample container 54.

The specimen quantitation section 27 comprises: a quantitation cylinder 27A; and a driving section 27B comprising a stepping motor for moving a quantitation piston inserted in the cylinder 27A in the up-and-down direction. The quantitation cylinder 27A is connected to the first pipette 26A via a direction switching valve V1 and by a pipe line.

The discrimination/substitution section 29 comprises: the substitution container 57 having an opening at the top; a piston 58 that can be moved in the up-and-down direction in the substitution container 57; and a driving section 59 comprising a stepping motor for moving the piston 58 in the substitution container 57 in the up-and-down direction.

The substitution container 57 is connected to a cleaning liquid unit 90 via switching valves V4 and V5 by a pipe line. Cleaning liquid is supplied from the cleaning liquid unit 90 via the switching valves V4 and V5 to the substitution container 57. The substitution container 57 is also connected to the diluting fluid unit 55 via a switching valve V6 and by a pipe line. Diluting fluid is supplied from the diluting fluid unit 55 via the switching valve V6 to the substitution container 57.

The piston 58 is composed of a hollow cylindrical body having a filter 60 at the lower part that doe not allow a to-be-measured cell (epidermal cell) to pass therethrough and that allows cells having a smaller diameter than that of the to-be-measured cell (e.g., red blood cell, white blood cell) to pass therethrough. The piston 58 is connected to a positive pressure source 71 as one embodiment of an analysis target peeling means via a switching valve V8 and by a pipe line. Thus, by releasing the switching valve V8, a positive pressure can be supplied to the interior of the piston 58. The piston 58 is configured so that the inner space of the piston 58 is connected via a switching valve V9 to the exterior. By releasing the switching valve V9, the inner space of the piston 58 can be released to air.

Furthermore, the piston 58 is connected via switching valves V10 and V12 to a filtrate disposal section 61 by a pipe line. Thus, the filtrate sucked from the interior of the piston 58 is disposed to the exterior through switching valves V10 and V12.

The piston 58 is also connected via a switching valve V7 to the cleaning liquid unit 90 by a pipe line. The cleaning liquid supplied from the cleaning liquid unit 90 is used to clean the piston 58 and the substitution container 57. The cleaning liquid used to clean the piston 58 and the substitution container 57 is discharged via switching valves V11 and V13 to the disposal section 61.

The reagent quantitation section 28 comprises: a pair of quantitation cylinders 28A and 28B; and a driving section 28C comprising a stepping motor for moving quantitation pistons inserted to the respective cylinders 28A and 28B in the up-and-down direction. The respective quantitation cylinders 28A and 28B are connected via supply switching valves V2 and V3 to the second pipette 26B by a pipe line. The reagent quantified by the respective quantitation cylinders 28A and 28B is supplied via supply switching valves V2 and V3 to the second pipette 26B and is discharged into the measurement sample container 54.

By the above configuration, a liquid sample including a to-be-measured cell having an increased concentration stored in the measurement sample container 54 of the specimen setting section 24 can be mixed with a plurality of reagents in predetermined amounts quantified by the reagent quantitation section 28.

In the present embodiment, there are two types of reagents quantified by the respective quantitation cylinders 28A and 28B of the reagent quantitation section 28. Among these reagents, the reagent that is measured by one quantitation cylinder 28A and that is added to a living body sample is staining liquid for performing PI staining. The reagent that is measured by the other quantitation cylinder 28B and that is added to the living body sample is RNase for subjecting cells to an RNA processing. The PI staining is performed by propidium iodide (PI) that is fluorescence staining fluid including dye. In the PI staining, a nucleus is selectively stained. Thus, the fluorescence from the nucleus can be detected. The RNA processing is a processing for dissolving RNA in the cell. The staining liquid stains both of the RNA and DNA of an epidermal cell. Thus, RNA is dissolved by performing the above RNA processing and is not stained by the staining liquid. Thus, the cell nucleus DNA can be measured accurately.

It is noted that the operations of the driving section of the respective sections and the switching valves (magnet valves) V1 to V13 shown in FIG. 7 and FIG. 8 are controlled based on a control instruction from the preparation control section 16 (the microprocessor 19).

[Configuration of Discrimination/Substitution Section]

Figure 9:
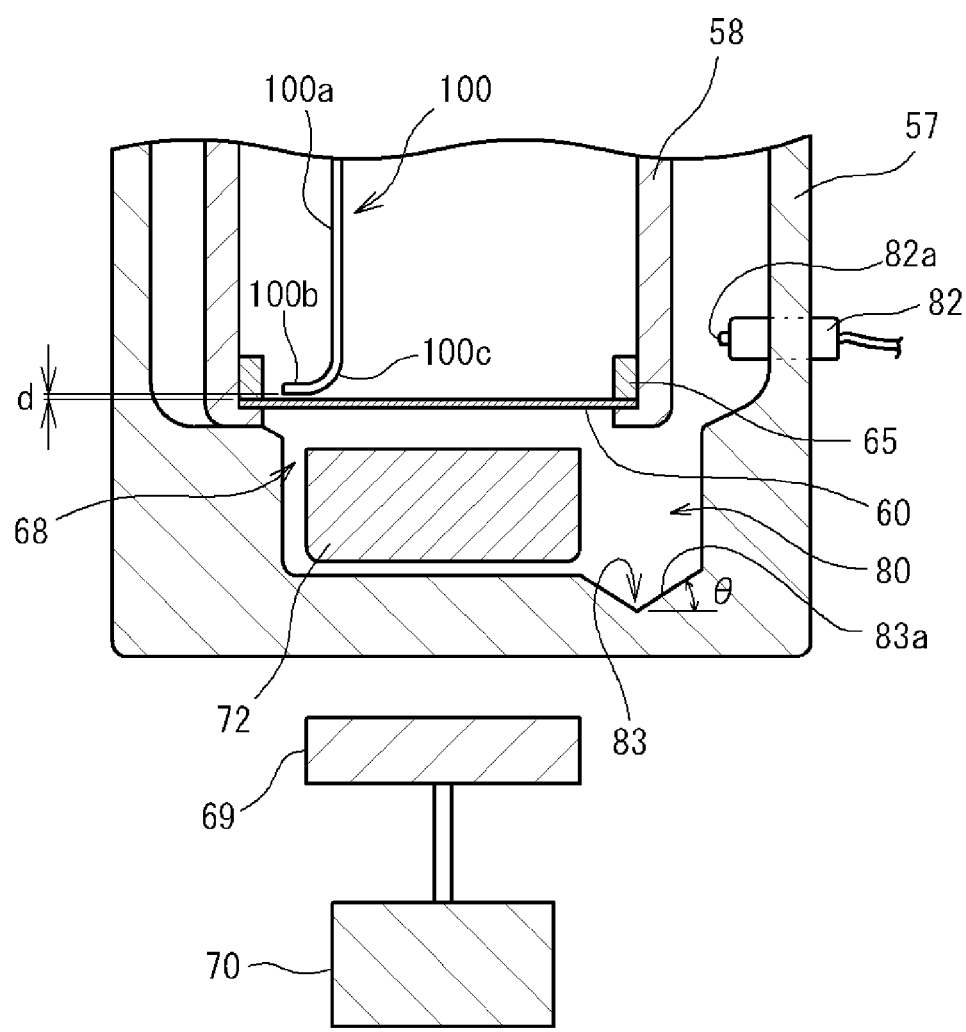
FIG. 9 is a cross-sectional view illustrating the neighborhood of a bottom section of a substitution container.

The following section will describe the configuration of the discrimination/substitution section 29 in the present embodiment with reference to FIG. 9. FIG. 9 is a cross-sectional view illustrating the neighborhood of the bottom section of the substitution container 57 in the discrimination/substitution section 29 of FIG. 8 in the present embodiment.

As shown in FIG. 9, the discrimination/substitution section 29 of the present embodiment comprises: the substitution container 57; the piston 58 composed of a cylindrical body movable in the substitution container 57 in the up-and-down direction; the filter 60 for selecting a to-be-measured cell provided at the lower end face of the piston 58 composed of a cylindrical body; a liquid level sensor 82 for sensing the liquid level of the liquid including the to-be-measured cell; and a suction tube 100 for sucking liquid including substance (non-analysis target) other than to-be-measured cells, the substance being selected via the filter 60.

The substitution container 57 comprises: a storage chamber 68 that can store therein an analysis target to be analyzed (to-be-measured cell); and a concentrated sample storage chamber 80 that is provided to communicate with the storage chamber. The storage chamber 68 stores therein a stirrer 72 (rotation member) for transporting the to-be-measured cell included in the liquid sample from the storage chamber 68 to the concentrated sample storage chamber 80. The stirrer 72 is configured to be rotated by a magnetic force. At the lower side of the bottom section of the storage chamber 68, there are provided a magnet 69 for providing a magnetic force to the stirrer 72 and a drive motor 70 for rotating the magnet 69.

Figure 10:
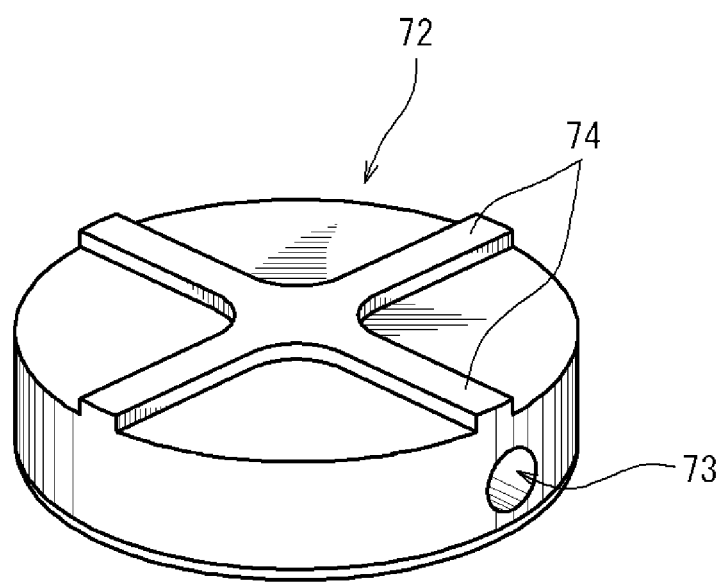
FIG. 10 is a perspective view illustrating one example of a stirrer.

The stirrer 72 has a short cylindrical shape and is made by trifluoroethylene (PCTFE) for example. FIG. 10 is a perspective view illustrating one example of the stirrer 72 in the present embodiment.

The circumference face of the stirrer 72 includes a hole 73 extending to the center. This hole 73 stores therein the round bar-like magnet. The upper face of the stirrer 72 has two ribs 74 intersecting to each other. The ribs 74 extend to the circumference edge. By forming the ribs 74 as described above, an improved efficiency can be provided to the agitation of the liquid sample existing between the lower face of the filter 60 and the upper face of the stirrer 72. As a result, the to-be-measured cell attached to the lower face of the filter 60 can be effectively peeled from the filter 60. At the same time, the to-be-measured cell can be effectively transported to the concentrated sample storage chamber which will be described later. The ribs 74 protrude with a height that is not particularly limited in the present invention but is generally about 0.3 to 1.0 mm.

Figure 11:
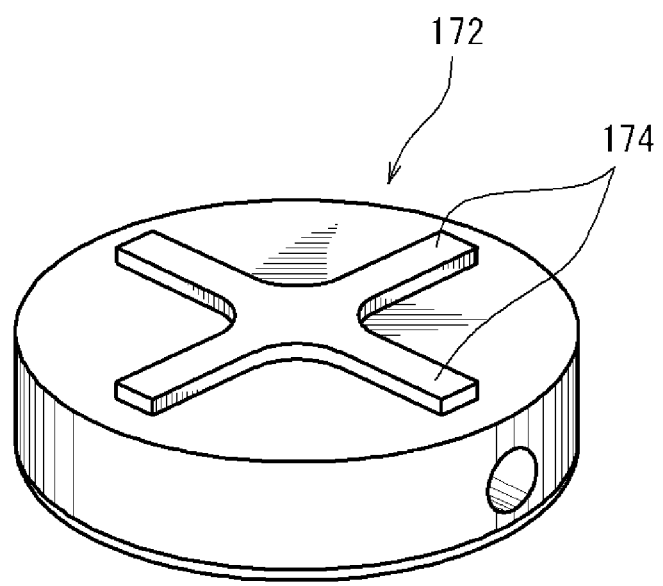
FIG. 11 is a perspective view illustrating another example of the stirrer.
Figure 12:
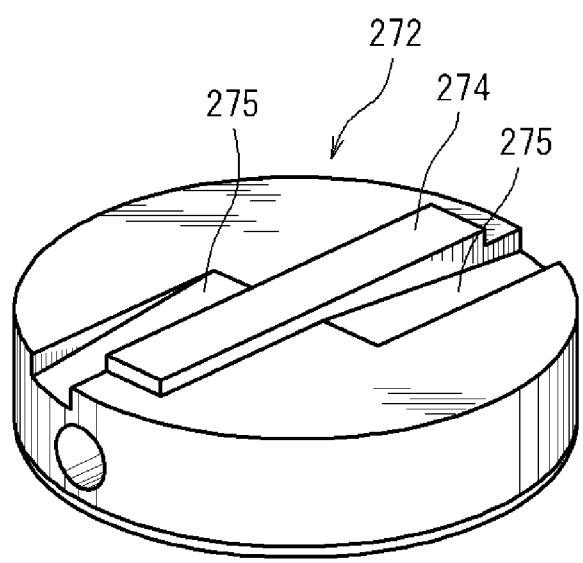
FIG. 12 is a perspective view illustrating still another example of the stirrer.

FIG. 11 is a perspective view illustrating a stirrer 172 according to another example. FIG. 12 is a perspective view illustrating a stirrer 272 according to still another example. The stirrer 172 shown in FIG. 11 is different from the stirrer 72 shown in FIG. 10 in that ribs 174 formed in the upper face do not extend to the circumference edge. The stirrer 272 shown in FIG. 12 is configured so that one rib 274 passing the center is formed at the upper face of the stirrer 272 and both sides of the rib 274 have slopes 275 inclined downwardly toward the circumference edge.

The distance between the lower face (filtering area) of the filter 60 and the upper faces of the ribs 74 of the stirrer 72 opposed to the lower face is not particularly limited but is preferably 1 mm or less and more preferably 0.6 mm or less. The rotation number of the magnet 69 for rotating the stirrer 72 (i.e., the rotation number of the drive motor 70) is preferably in a range from 1000 to 2000 rpm and is more preferably about 1300 rpm.

Referring to FIG. 9 again, the piston 58 is configured so that the bottom section thereof has the filter 60 via a retainer 65. The piston 58 functions as a liquid separation section that allows liquid to pass through the filter 60 to thereby separate the liquid to the first liquid mainly including a to-be-measured cell and the second liquid mainly including cells having a smaller diameter than that of the to-be-measured cell.

The suction tube 100 is provided in the piston 58. The suction tube 100 is composed of: a longitudinal tube 100*a* having a tube axis parallel to the axis of the piston 58; a lateral tube 100*b* that is provided at a tip end of the longitudinal tube 100*a* and that has a tube axis substantially orthogonal to the tube axis of the longitudinal tube 100*a*; and a curved tube 100*c* connecting the longitudinal tube 100*a* to the lateral tube 100*b*. The suction tube 100 is provided in the piston 58 so that the tube axis of the lateral tube 100*b* at the tip end thereof is substantially parallel to the filter face. The distance d between the lower end of the lateral tube 100*b* and the filter face is set to a range from 0.1 to 3 mm (e.g., 0.5 mm). The other end of the suction tube 100 is connected to a negative pressure source (not shown). By driving the negative pressure source, the first liquid including cells (red blood cells, white blood cells) having a smaller diameter than that of the to-be-measured cell (epidermal cell) can pass through the filter 60 and the liquid can be sucked from the tip end of the lateral tube 100*b*. The sucked liquid is discharged to the outside via the switching valves V10, V12.

When the liquid is sucked by the lateral tube 100*b* positioned substantially parallel to the filter face as in the present invention, the filter 60 does not clog up the suction opening at a tip of the suction tube 100, so that the liquid in the piston 58 can be sucked efficiently.

In the present embodiment, it is assumed that the to-be-measured cell is an epidermal cell of a cervix. This epidermal cell has a size of about 20 to 80 μm (and an average size of about 60 μm). Red blood cells, which are cells having a smaller size than that of the to-be-measured cell as described above, have a size of about 7 to 10 μm. White blood cells, which are also cells having a smaller size than that of the to-be-measured cell, have a size of about 8 to 15 μm. Impurities such as bacteria have a size of about 1 to a few μm.

In view of the above, in order to prevent an epidermal cell from passing the through hole of the filter 60 to move into the piston 58 even when the liquid in the substitution container 57 receives a pressure, the filter 60 in the present embodiment is a metal CVD (Chemical Vapor Deposition) filter with a through hole having a diameter of 8 to 20 μm. The metal CVD filter as described above has an advantage in that the through hole is suppressed from being deformed when compared with other resin-made filters and the metal mesh ones, thus improving the aperture ratio.

Furthermore, the reason why the hole diameter of the filter 60 is set to 8 to 20 μm is that a diameter smaller than 8 μm frequently shows a phenomenon where the through hole is clogged with a cell or foreign substance at an early stage and a diameter exceeding 20 μm on the other hand frequently causes an epidermal cell to undesirably pass through a through hole when a pressure is applied to the liquid in the storage container 57. It is noted that the hole of the filter 60 preferably has a diameter of about 10μ.

The liquid level sensor 82 as liquid level sensing means is provided at the lower part of the substitution container 57 in order to sense the liquid level of the first liquid in the substitution container 57. The liquid level sensor 82 is a capacitance-type one in which a tip end protrudes by about 2 to 3 mm to the inner side from the inner face of the substitution container 57. The tip end of the protruded part has a pin-like sensor section 82*a*.

The liquid level sensor 82 is used to sense that the liquid level of the first liquid including the to-be-measured cell reaches the position at substantially the lower face of the filter 60.

In the present embodiment, the sensor section 82*a* is provided at a position about 2.0 mm above the lower face of the filter 60. In consideration of the influence by the surface tension and the speed at which the second liquid is sucked, the suction of the second liquid in the piston 58 is stopped when a predetermined time has passed since the reception of a sensing signal from the sensor section 82*a*. By providing the pin-like sensor section 82*a* at an obliquely-upward direction, liquid can be removed more quickly to thereby improve the accuracy of the sensing of liquid level. The pin-like sensor section 82*a* is provided at an angle to the horizontal plane in a range of about 5 to 90 degrees.

In the present embodiment, the bottom section of the substitution container 57 has: the storage chamber 68; and the concentrated sample storage chamber 80 provided to communicate with the circumference edge of the storage chamber 68. The concentrated sample storage chamber 80 has a function to collect the to-be-measured cell transported by the rotation of the stirrer 72 stored in the storage chamber 68. By a discrimination operation which will be described later, a part of the to-be-measured cell is attached to the lower face of the filter 60. The attached to-be-measured cell is peeled by the rotation of the stirrer 72 from the lower face of the filter 60. Then, the to-be-measured cell is collected by the centrifugal force generated by the rotation of the stirrer 72 into the concentrated sample storage chamber 80 provided to communicate with the circumference edge of the storage chamber 68. The stirrer 72, and the above-mentioned magnet 69 and the drive motor 70 constitute another embodiment of the analysis target peeling means for peeling the analysis target from the lower side of the filter.

Figure 13:
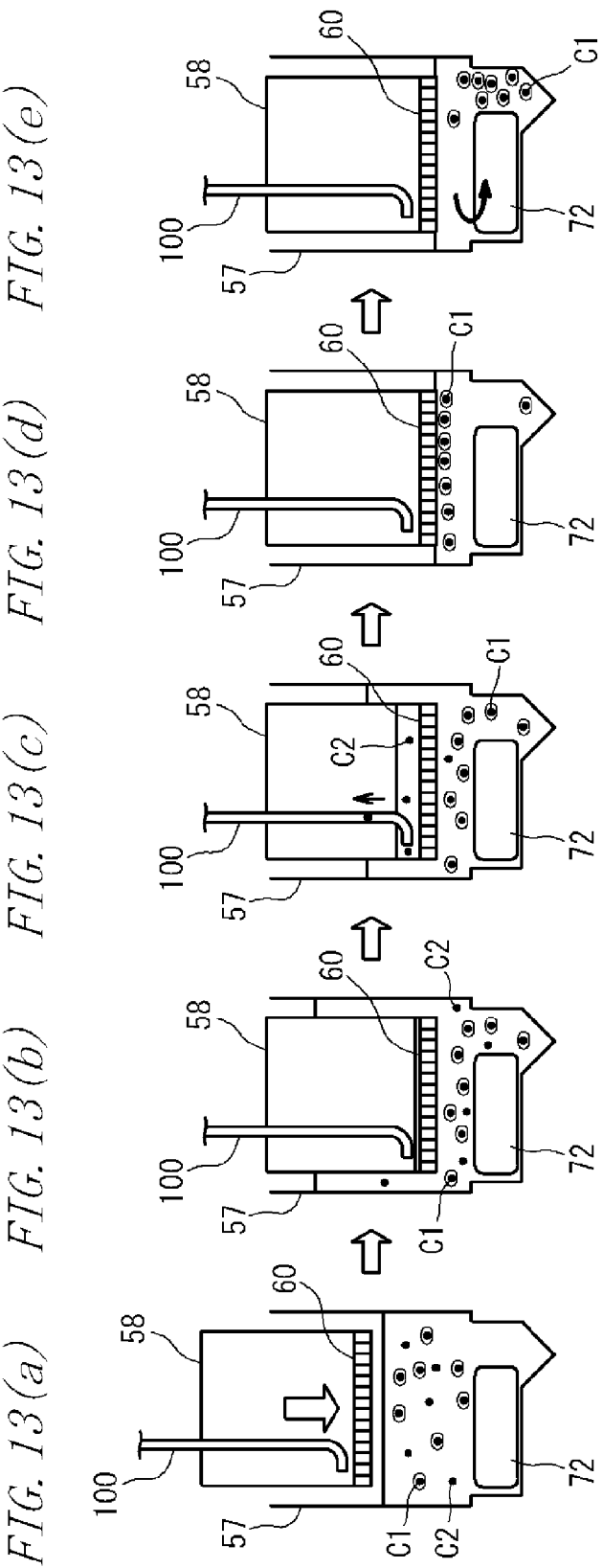
FIG. 13 is a schematic view illustrating the concentration process of an analysis target in a discrimination/substitution section.

The following section will describe in detail a process in the present embodiment to discriminate the mixed liquid of the living body sample and the preservative solution to prepare, from a liquid sample including to-be-measured cell thus discriminated, a liquid sample including the to-be-measured cell having a higher concentration with reference to a schematic view of FIG. 13.

First, as shown in FIG. 13(*a*), the piston 58 is moved downwardly so that the filter 60 moves from the upper side of the liquid level of the mixed liquid of the living body sample and the preservative solution in the substitution container 57 into the liquid. In this stage, the interior portion of the substitution container 57 is under an open condition communicating with the atmosphere and the inside of the piston 58 is under a sealed condition in which communication with the atmosphere is interrupted by the valve operation.

Then, as shown in FIG. 13(*b*), the liquid level of the mixed liquid in the substitution container 57 rises by the approach of the piston 58. Further, a small amount of the mixed liquid moves into the piston 58 through the filter 60.

Then, as shown in FIG. 13(*c*), by driving the negative pressure source to make a pressure in the piston 58 negative through the suction tube, the mixed liquid in the substitution container 57 communicating with the atmosphere moves into the piston 58 through the filter 60 due to a differential pressure. In that case, since the size of a through hole of the filter 60 is set to be smaller than that of the to-be-measured cell as stated above, the liquid including the to-be-measured cell (C1) (the first liquid) remains at the lower part of the filter 60 in the substitution container 57, while the liquid including cells having a smaller diameter than that of the to-be-measured cell (C2) (the second liquid) moves above the filter 60 (inside the piston 58). Then, the liquid including cells having a smaller diameter than that of the to-be-measured cell (C2) is sucked by the suction tube 100 to be discharged to the outside of the storaged chamber.

Thereafter, the driving of the negative pressure source is stopped when the liquid level sensor 82 (see FIG. 9) senses that the liquid level of the first liquid including the to-be-measured cell reaches approximately the lower face of the filter 60 (see FIG. 13(*d*)). In the present embodiment, a negative pressure is applied to the inside of the piston 58 via the suction tube 100 to thereby move the second liquid to the inside of the piston 58 and discharge the second liquid to the outside. Thus, a part of the to-be-measured cells (C1) included in the first liquid is attached to a lower side of the filter 60.

Then, as shown in FIG. 13(*e*), the stirrer 72 is rotated to thereby peel the to-be-measured cell attached to the lower side of the filter 60 and to store the to-be-measured cell included in the first liquid in the concentrated sample storage chamber. By acquiring the liquid including the to-be-measured cell stored in the concentrated sample storage chamber, a measurement sample including the to-be-measured cell having a high concentration can be obtained.

The concentrated sample storage chamber 80 has, at the bottom section thereof, a taper section 83 having a gradually-decreasing cross-sectional area toward the lower side. The liquid sample stored in the concentrated sample storage chamber 80 is sucked by the first pipette 26A as a liquid acquisition section by lowering the tip end of the first pipette 26A to the neighborhood of the tip end of the taper section 83 to thereby suck the liquid sample from the neighborhood of the tip end. As a result, the liquid sample in the concentrated sample storage chamber 80 can be sucked as much as possible without waste.

The inclined surface 83*a* constituting the taper section 83 has the inclination angle θ to the horizontal plane that is not particularly limited in the present invention. However, in consideration of the bore of the tip end of the first pipette 26A for example, the inclination angle θ is generally in a range from 5 to 45 degrees. The concentrated sample storage chamber 80 has horizontal cross section and size (cross-sectional area) that can be selected in consideration of the amount of a liquid sample required for the measurement and a predetermined yield.

Figure 14:
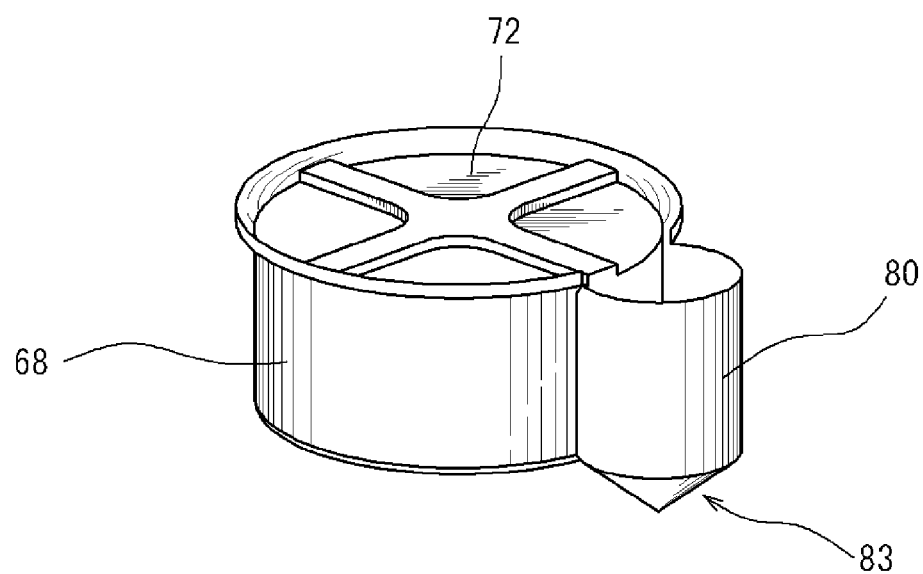
FIG. 14 illustrates one example of a concentrated sample storage chamber.
Figure 15:
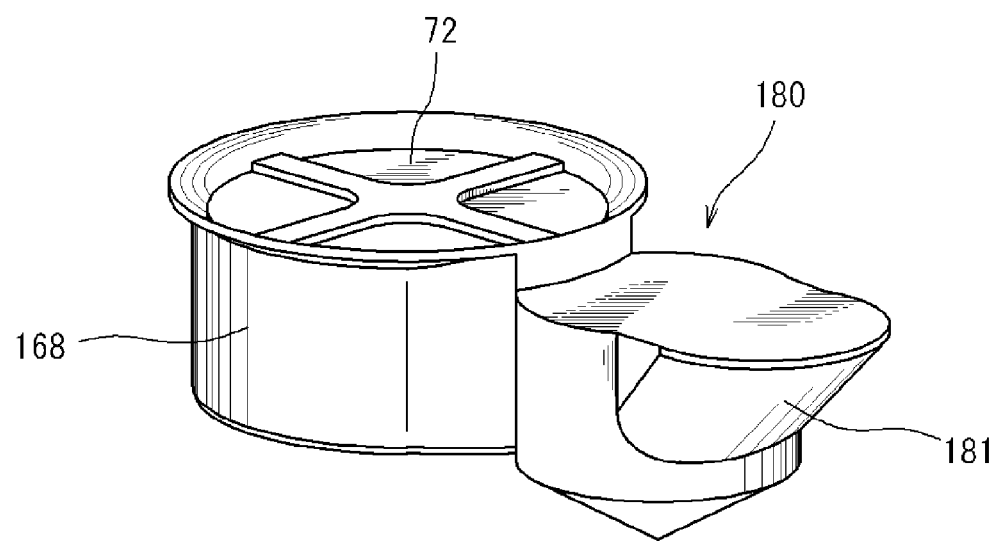
FIG. 15 illustrates another example of the concentrated sample storage chamber.
Figure 16:
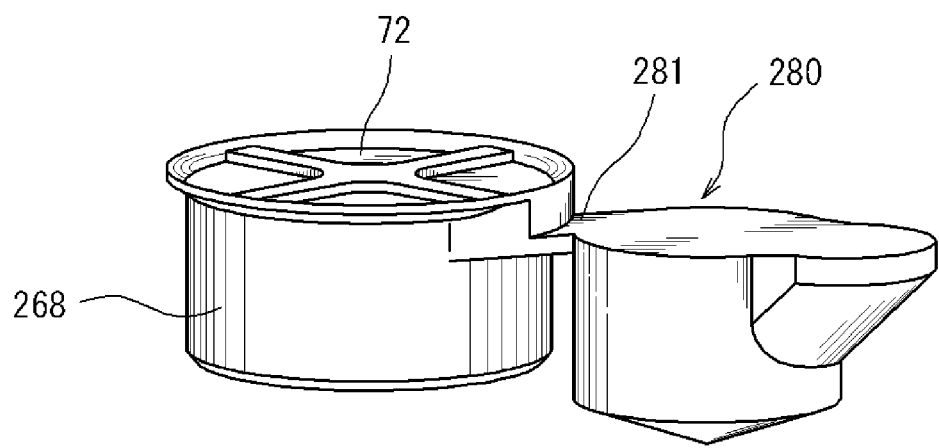
FIG. 16 illustrates still another example of the concentrated sample storage chamber.

FIG. 14 is a schematic view illustrating the storage chamber 68 and the concentrated sample storage chamber 80. The concentrated sample storage chamber 80 is provided to communicate with the circumference edge of the storage chamber 68. The storage chamber 68 stores therein the stirrer 72. FIG. 15 to FIG. 16 illustrate other shapes of the concentrated sample storage chamber 80. The concentrated sample storage chamber 180 shown in FIG. 15 has a bulge portion 181 to the outer side in the diameter direction. The upper part of the bulge portion 181 has the above-described capacitance-type liquid level sensor 82. By the configuration as described above, when the liquid sample is sucked from the concentrated sample storage chamber 180, the first pipette 26A can be inserted from the upper part of the concentrated sample storage chamber 180 to the taper section 183 without being blocked by the liquid level sensor 82.

The concentrated sample storage chamber 280 shown in FIG. 16 communicates with the storage chamber 268 via a communication path 281. The storage chamber 268 stores therein the stirrer 72. The communication path 281 is provided along the tangential direction of the storage chamber 268 composed of a cylindrical body. More particularly, the communication path 281 is provided, with regard to the rotation direction of the stirrer 72, along the tangential direction along which the centrifugal force by the rotation acts. Thus, the to-be-measured cell transported by the stirrer 72 is easily stored in the concentrated sample storage chamber 280 along the communication path 282. The communication path 281 can be, for example, a path having a rectangular cross section having a width of 1.0 to 5.0 mm and a depth of about 1.0 to 3.0 mm.

[Processing Operation]

Next, the following section will describe the processing operation of the cell analyzer 1 as described above.

Figure 17:
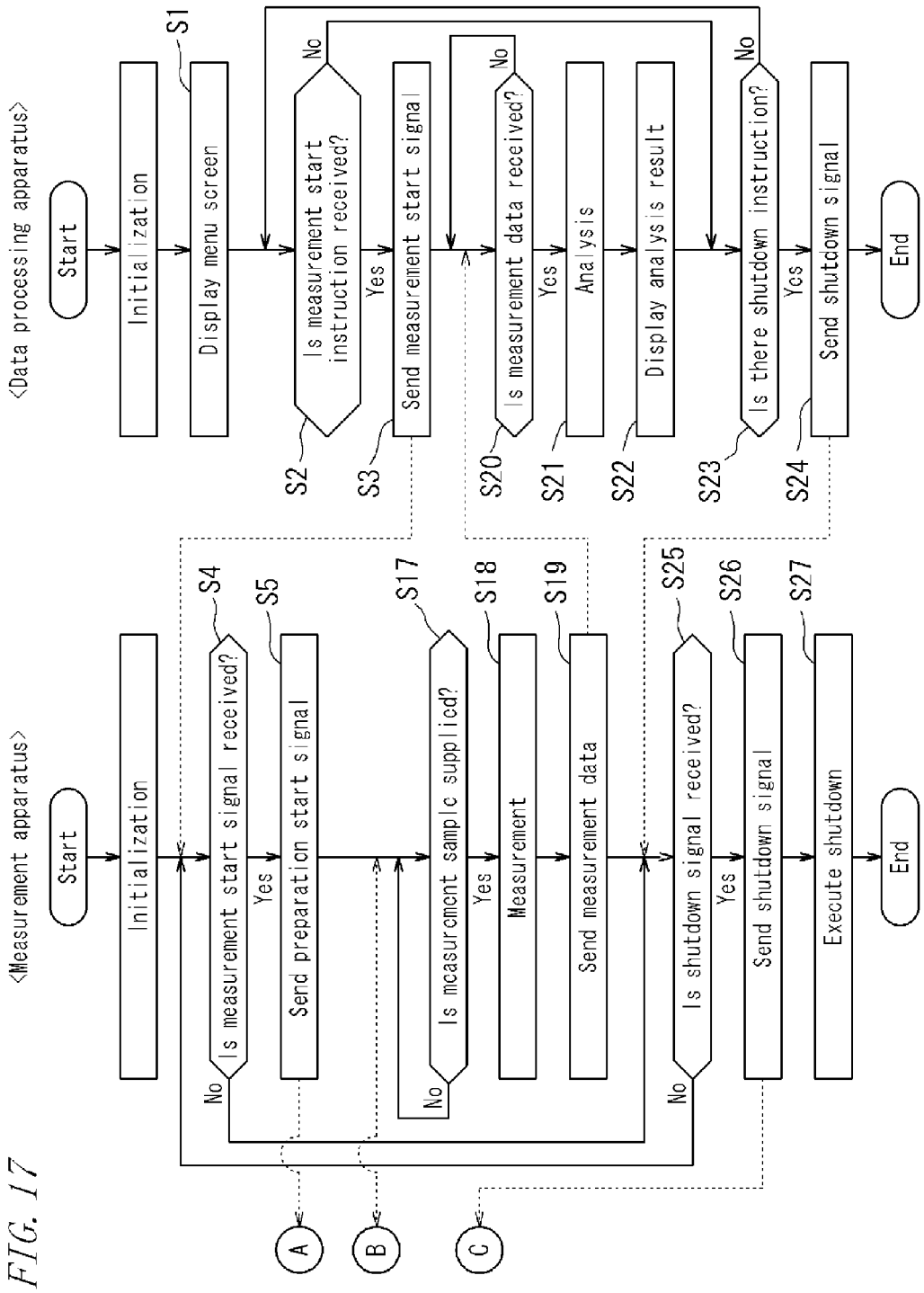
FIG. 17 is a flowchart illustrating the processings performed by the respective control sections of the cell analyzer.
Figure 18:
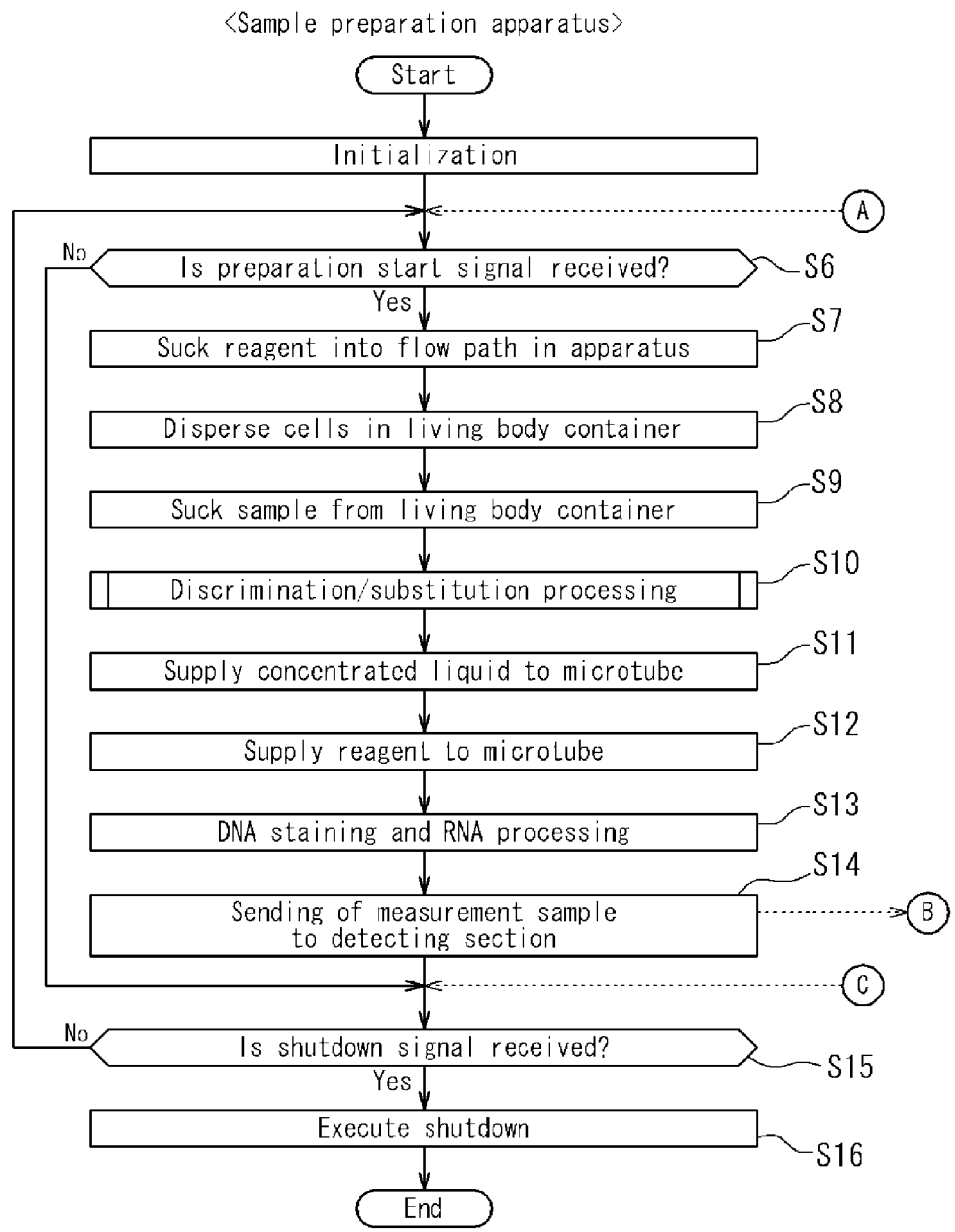
FIG. 18 is a flowchart illustrating the processings performed by the respective control sections of the cell analyzer.

FIG. 17 and FIG. 18 are a flowchart illustrating the processings performed by the respective control sections 8, 16, and 31 of the cell analyzer 1.

It is noted that FIG. 17 shows, at the right column, a processing flow performed by the control section (processing body) 31 of the data processing apparatus 4 and shows, at the left column, a processing flow performed by the control section 8 of the measurement apparatus 2. FIG. 18 shows a processing flow performed by the control section 16 of the sample preparation apparatus 3 in a single column. However, this processing flow is connected to the processing flow of FIG. 17 at the shown points A, B, and C. The following section will describe, with reference to FIG. 17 and FIG. 18, the processing contents performed by the cell analyzer 1.

First, the control section 31 of the data processing apparatus 4 causes the display section 32 to display a menu screen (Step S1). Thereafter, upon accepting a measurement starting instruction based on the menu screen from the input section 33 (Step S2), the control section 31 of the data processing apparatus 4 sends a measurement starting signal to the measurement apparatus 2 (Step S3).

Upon receiving the measurement starting signal (Step S4), the control section 8 of the measurement apparatus 2 sends a preparation starting signal to the sample preparation apparatus 3 (Step S5 and point A).

Upon receiving the preparation starting signal (Step S6), the control section 16 of the sample preparation apparatus 3 sucks the reagent (staining fluid, RNase) used to prepare a measurement sample into a flow path in the apparatus and disperses, in the cell dispersion section 25, the cells in the mixed liquid of the living body sample and preservative solution including methanol as a major component contained in the living body container 53 (Steps S7 and S8).

Thereafter, the control section 16 of the sample preparation apparatus 3 causes the already-dispersed mixed liquid to be sucked by a predetermined amount from the living body container 53 into the flow path in the apparatus (Step S9) and causes the liquid to be sent to the storage container 57 of the discrimination/substitution section 29. Then, the discrimination/substitution section 29 is caused to perform a discrimination/substitution processing to the mixed liquid of the living body sample and the preservative solution (Step S10).

[Contents of Discrimination/Substitution Processing]

Figure 19:
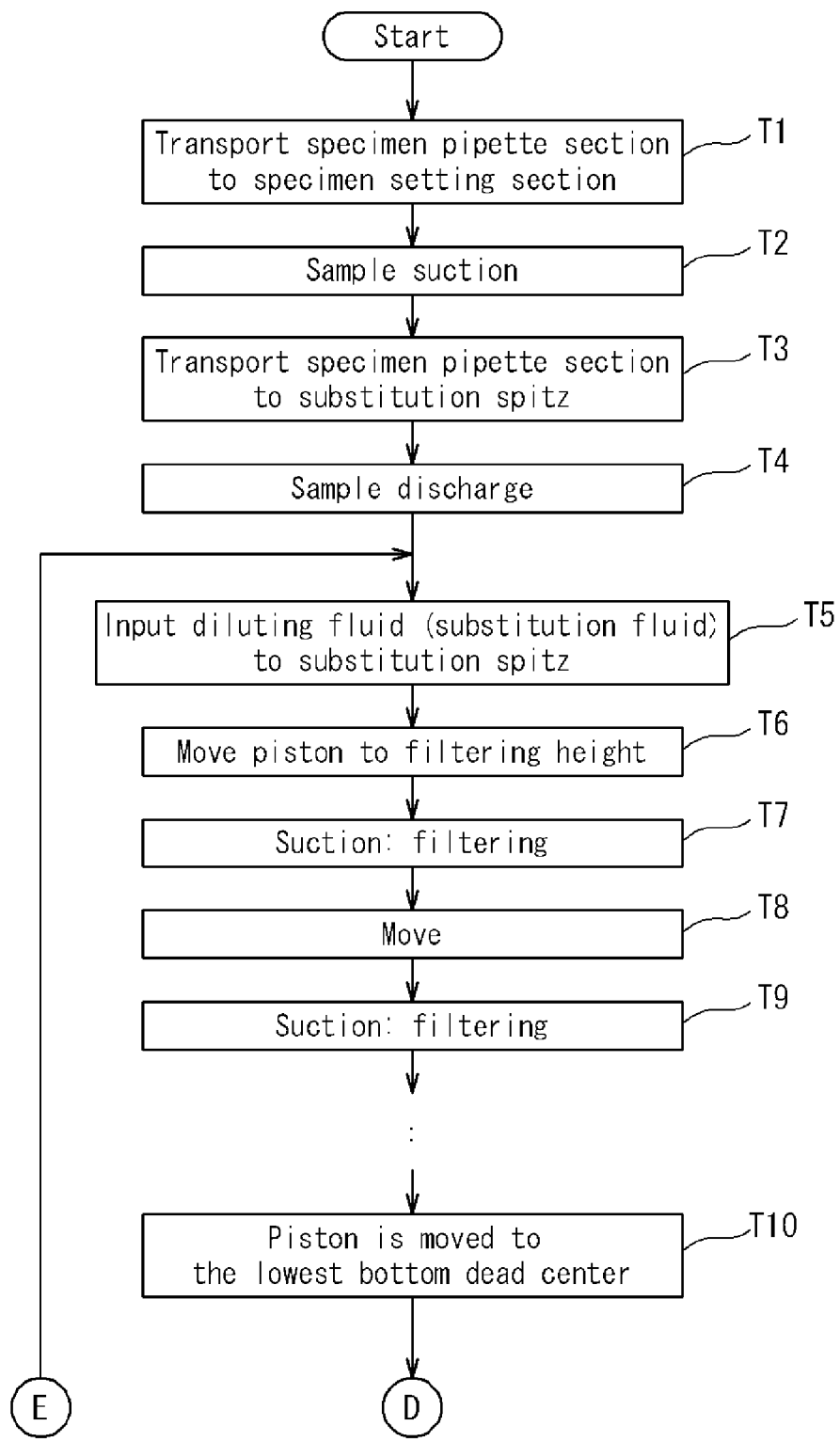
FIG. 19 is a flowchart illustrating a discrimination/substitution processing.
Figure 20:
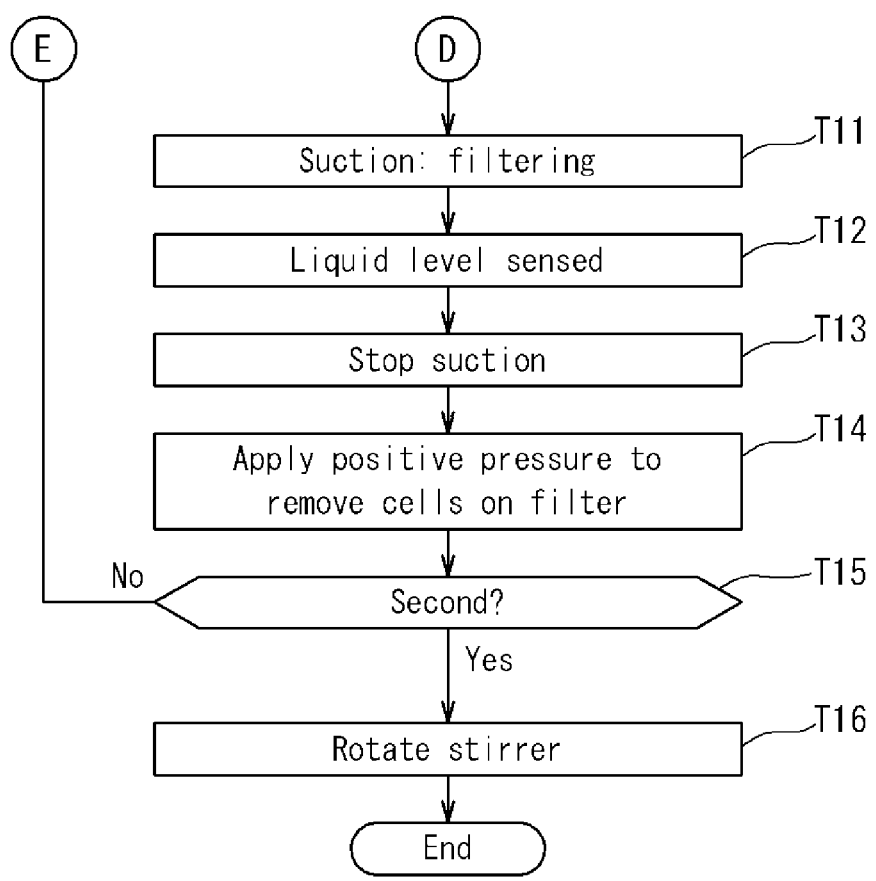
FIG. 20 is a flowchart illustrating a discrimination/substitution processing.

FIG. 19 to FIG. 20 are a flowchart illustrating the discrimination/substitution processing (Step S10).

As shown in FIG. 19, a control section 16 of the sample preparation apparatus 3 firstly transports the specimen pipette section 26 to the specimen setting section 24 (Step T1) and causes the first pipette 26A to suck the sample (liquid sample) in the living body container 53 set in the rotation table 24A (Step T2).

Next, the control section 16 transports the specimen pipette section 26 to the substitution container 57 (Step T3) and causes the sample sucked in the first pipette 26A to be discharged to the substitution container 57 (Step T4).

Next, diluting fluid (substitution fluid) is inputted to the interior of the substitution container 57 from the diluting fluid unit 55 via the valve V6 (Step T5).

Next, the piston 58 is moved downwardly by the driving section 59 to a predetermined filtering height (Step T6). Then, the sample in the substitution container 57 is sucked into the piston 58 and is filtered (Step T7). The suction and filtering is carried out by the valves V10 and V12 connected to a relief valve set to −7 kpa. As a result, the suction and filtering causes a pressure of about −3 kpa to be applied to the filter 60 provided at the lower end of the piston 58. By sucking and filtering the liquid by such a weak negative pressure, the filtering can be carried out while preventing the to-be-measured cell from passing through the filter 60 to be discharged to the disposal section 61.

Next, the piston 58 is further moved downwardly by the driving section 59 (Step T8). Then, as in Step T7, the sample in the substitution container 57 is sucked into the piston 58 and is filtered (Step T9).

The traveling of the piston 58 and the suction and filtration of the sample as described above are repeated a predetermined number of times and the piston 58 moves to the predetermined lowest bottom dead center (Step T10). Then, as in Step T7, the sample in the substitution container 57 is sucked and filtered into the piston 58 (Step T11). Then, when the sensor section 82a of the capacitance-type liquid level sensor 82 positioned in the substitution container 57 senses the liquid level (Step T12), the suction is stopped after the passage of a predetermined time (Step T13). At this stage, the storage chamber 68 and the concentrated sample storage chamber 80 provided in the bottom section of the substitution container 57 are filled with the liquid sample including the to-be-measured cell.

Next, a positive pressure is applied to the interior of the piston 58 in order to remove the cell (analysis target) filled in the through hole of the filter 60 or attached to the lower face of the filter 60 to return the cell into the substitution container 57 (or into the storage chamber 68 and the concentrated sample storage chamber 80) (Step T14).

Then, the control section 16 of the sample preparation apparatus 3 determines whether the travelling of the piston 58 to the lowest bottom dead center is the second one or not (Step T15).

The control section 16 of the sample preparation apparatus 3 repeats, when the travelling of the piston 58 to the lowest bottom dead center is not the second one, the filtering process from the input of the diluting fluid to a substitution spitz (Step T5). When the travelling of the piston 58 to the lowest bottom dead center is the second one, the processing proceeds to Step T16.

In Step T16, the drive motor 70 causes the magnet 69 to rotate to thereby rotate the stirrer 72. This consequently removes the to-be-measured cell attached to the lower face of the filter 60. At the same time, the to-be-measured cell included in the liquid sample in the storage chamber 68 is transported to the concentrated sample storage chamber 80 and the to-be-measured cell is stored in the concentrated sample storage chamber 80 (Step T16).

By the discrimination/substitution processing, there can be acquired such liquid that mainly includes the to-be-measured cell (epidermal cell) and that includes a reduced number of cells other than the to-be-measured cell. Furthermore, by the above discrimination/substitution processing, the concentration of the preservative solution in the liquid (the mixed liquid of the living body sample and the preservative solution) supplied from the living body container 53 to the substitution container 57 can be reduced by substituting the most part of the preservation solution with the diluted solution. Thus, in a DNA staining processing which will be described later, the influence by the preservative solution can be reduced and the DNA of the to-be-measured cell can be stained favorably.

Furthermore, in the discrimination/substitution processing, the substitution processing of the preservative solution and the diluted solution can be performed while the cell discrimination processing is being performed. Thus, the discrimination processing and the substitution processing can be performed with a shorter time when compared with a case where these two processings are performed separately.

Furthermore, in the discrimination/substitution processing, the stirrer 72 is rotated to peel off the to-be-measured cell (epidermal cell) attached to the lower face of the filter 60 by a shearing force to float the to-be-measured cell in the first liquid at the lower side of the filter 60. A pressure is applied from the upper side of the filter 60 to the through hole of the filter 60 to thereby remove the to-be-measured cell (epidermal cell) clogging the through hole of the filter 60, thus allowing the to-be-measured cell to float in the first liquid at the lower side of the filter 60. Thus, the to-be-measured cell (epidermal cell) attached to the filter can be efficiently collected without loss.

Furthermore, in the present embodiment, the concentrated sample storage chamber 80 is provided at the circumference edge of the storage chamber 68 to have communication therewith. Thus, by the rotation of the stirrer 72, the to-be-measured cell included in the liquid sample in the storage chamber 68 is collected in the concentrated sample storage chamber 80. As a result, the to-be-measured cell included in the liquid sample in the storage chamber 68 has a lower concentration and the to-be-measured cell included in the liquid sample in the concentrated sample storage chamber 80 has a higher concentration. Thus, by acquiring the liquid sample from the concentrated sample storage chamber 80 as described above, the measurement sample having a higher concentration of the to-be-measured cell can be acquired.

[Preparation of Measurement Sample]

Next, the control section 16 of the sample preparation apparatus 3 causes the specimen pipette section 26 to be transported to the substitution container 57 and causes the concentrated sample to be sucked from the concentrated sample storage chamber 80 into the first pipette 26A. Furthermore, the control section 16 causes the specimen pipette section 26 to be transported to the specimen setting section to thereby supply the concentrated sample to a measurement sample container (microtube) 54 (Step S11).

Next, the control section 16 of the sample preparation apparatus 3 causes the staining fluid and the RNase stored in the apparatus to be sent from the reagent quantitation section 28 to the second pipette 26B. This second pipette 26B causes the sent staining fluid and RNase to be supplied to the measurement sample container 54 (Step S12). In the measurement sample container 54, DNA staining and RNA processing are caused to be performed to thereby prepare a measurement sample (Step S13).

After the processing, the resultant measurement sample is quantified via the first pipette 26A by the specimen quantitation section 27. After the quantitation, the sample is supplied to the detection section 6 of the measurement apparatus 2 (Step S14 and point B).

The control section 16 of the sample preparation apparatus 3 always determines whether a shutdown signal from the measurement apparatus 2 is received or not (Step S15 and point C). When the signal is not received, the processing returns to Step S6 to determine whether a preparation start signal is received or not. When the signal is received, a shutdown processing is carried out to thereby complete the sample preparation processing (Step S16).

[Measurement by Measurement Apparatus and the Data Analysis Thereof]

Referring back to FIG. 17, the control section 8 of the measurement apparatus 2 always determines, after sending a preparation start signal, whether a measurement sample is supplied from the sample preparation apparatus 3 or not (Step S17).

When the measurement sample is sent from the sample preparation apparatus 3 (point B), the control section 8 of the measurement apparatus 2 causes the measurement sample to be sent to a flow cell 45 of the measurement section 14. The control section 8 carries out the measurement with regard to the cell in the measurement sample (Step S18) and sends the measurement data to the data processing apparatus 4 (Step S19).

On the other hand, the control section 31 of the data processing apparatus 4 always determines, after sending the measurement starting signal, whether the measurement data is received from the measurement apparatus 2 or not (Step S20).

Upon receiving the above measurement data from the measurement apparatus 2, the control section 31 of the data processing apparatus 4 uses the measurement data to analyze the cell or nucleus to determine whether the cell in the measurement sample is cancerous or not for example (Step S21).

The control section 31 of the data processing apparatus 4 causes the above analysis result to be displayed on the display section 32 (Step S22) and determines whether there is a shutdown instruction by user input or not (Step S23).

When there is the above shutdown instruction, the control section 31 of the data processing apparatus 4 sends a shutdown signal to the measurement apparatus 2 (Step S24).

The control section 8 of the measurement apparatus 2 always determines whether the above shutdown signal from the data processing apparatus 4 is received or not (Step S25). When the signal is not received, the processing returns to Step S4 for determining whether a measurement starting signal is received or not. When the signal is received, the above shutdown signal is transferred to the sample preparation apparatus 3 (Step S26) and the shutdown is executed to thereby complete the measurement processing (Step S27).

As described above, according to the cell analyzer 1 of the present embodiment, the liquid mainly including a cell having a larger diameter is acquired as liquid. This consequently eliminates the need for an operation to separate a to-be-measured cell captured on a filter from the filter to collect the cell for example. Thus, the to-be-measured cell can be collected easily by rotating the stirrer 72 to transport the to-be-measured cell to the interior of the concentrated sample storage chamber 80. As a result, the to-be-measured cell included in the liquid sample in the storage chamber 68 has a lower concentration and the to-be-measured cell included in the liquid sample in the concentrated sample storage chamber 80 has a higher concentration. Thus, by acquiring the liquid sample from the concentrated sample storage chamber 80, a liquid sample including a to-be-measured cell having a higher concentration can be obtained. As a result, an increased number of to-be-measured cells can be obtained without increasing the amount of measurement samples to thereby improve the measurement accuracy.

Second Embodiment

Next, the following section will describe the second embodiment of the sample preparation apparatus of the present invention. The sample preparation apparatus according to the second embodiment is similar to the above-described sample preparation apparatus 3 according to the first embodiment in comprising: a preparation control section; an I/O interface; and a preparation device section for automatically adjusting the components of a living body sample. The sample preparation apparatus according to the second embodiment has the same configuration as that of the sample preparation apparatus 3 according to the first embodiment except for that a discrimination/substitution section as a component of the preparation device section has a different configuration from that of the discrimination/substitution section 29 of the first embodiment. Therefore, the same configurations as those of the first embodiment will be denoted with the same reference numerals and will not be described further.

[Configuration of Discrimination/Substitution Section]

Figure 21:
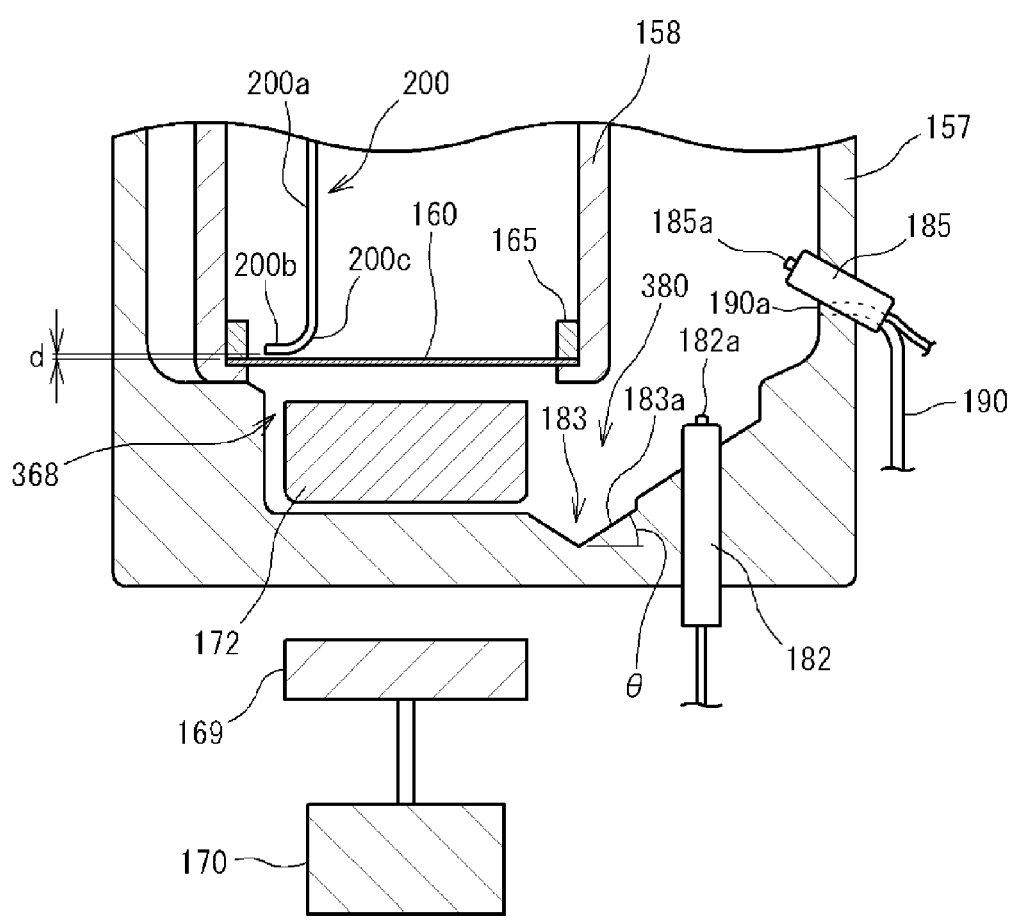
FIG. 21 is a cross-sectional view illustrating the neighborhood of a bottom section of a substitution container in a sample preparation apparatus according to another embodiment.

The following section will describe the configuration of the discrimination/substitution section in the second embodiment with reference to FIG. 21. FIG. 21 is a cross-sectional view illustrating the neighborhood of the bottom section of a substitution container 157 in the discrimination/substitution section in the second embodiment. FIG. 21 corresponds to FIG. 9 illustrating the substitution container 57 in the first embodiment.

As shown in FIG. 21, the discrimination/substitution section of this embodiment comprises: the substitution container 157; a piston 158 composed of a cylindrical body that is movable in the substitution container 157 in the up-and-down direction; a filter 160 for selecting to-be-measured cell that is provided at the lower end face of the piston 158 composed of a cylindrical body; a lower second liquid level sensor 182 for sensing the liquid level of the liquid including the to-be-measured cell; an upper first liquid level sensor 185 that is provided above the second liquid level sensor 182 and above the filter 160 by a predetermined distance and that is used to suppress a cell from being attached to the filter lower face (which will be described later); and a suction tube 200 for sucking liquid including substances other than the to-be-measured cell (non-analysis target) selected via the filter 160. The first liquid level sensor 185 and the second liquid level sensor 182 configure a liquid level sensing means for sensing the liquid level of a liquid sample. At the tip ends of the first liquid level sensor 185 and the second liquid level sensor 182, there are provided a sensor section 185a and a sensor section 182a each having a pin-like shape, respectively.

In the present embodiment, in the vicinity of the first liquid level sensor 185 (the back side of the first liquid level sensor 185 in FIG. 21), a substitution fluid blowout tube 190 is provided through which substitution fluid can be blown into the substitution container 157. A tip end of the substitution fluid blowout tube 190 is open in the substitution container 157.

The substitution container 157 comprises: a storage chamber 368 that can store therein an analysis target to be analyzed (to-be-measured cell); and a concentrated sample storage chamber 380 provided to communicate with the storage chamber. The storage chamber 368 stores therein a stirrer 172 (rotation member) for transporting a to-be-measured cell included in a liquid sample from the storage chamber 368 to the concentrated sample storage chamber 380. This stirrer 172 is configured to be rotated by a magnetic force. At the lower side of the bottom section of the storage chamber 368, there are provided a magnet 169 for providing a magnetic force to the stirrer 172 and a drive motor 170 for rotating the magnet 169.

The piston 158 has, at the bottom section thereof, the filter 160 via a retainer 165. The piston 158 functions as a liquid separation section that allows liquid to pass through the filter 160 to thereby separate the liquid to the first liquid mainly including a to-be-measured cell and the second liquid mainly including cells having a smaller diameter than that of the to-be-measured cell.

The suction tube 200 is provided in the piston 158. The suction tube 200 is composed of: a longitudinal tube 200a having a tube axis parallel to the axis of the piston 158; a lateral tube 200b that is provided at a tip end of the longitudinal tube 200a and that has a tube axis substantially orthogonal to the tube axis of the longitudinal tube 200a; and a curved tube 200c connecting the longitudinal tube 200a to the lateral tube 200b. The suction tube 200 is provided in the piston 158 so that the tube axis of the lateral tube 200b at the tip end thereof is substantially parallel to the filter face. The distance d between the lower end of the lateral tube 200b and the filter face is set to a range from 0.1 to 3 mm (e.g., 0.5 mm). The other end of the suction tube 200 is connected to a negative pressure source (not shown). By driving the negative pressure source, the first liquid including cells (red blood cells, white blood cells) having a smaller diameter than that of the to-be-measured cell (epidermal cell) can pass through the filter 60 and the liquid can be sucked from the tip end of the lateral tube 200b.

The concentrated sample storage chamber 380 in the present embodiment is also configured, as in the concentrated sample storage chamber 80 in the first embodiment, so that the bottom section thereof has a taper section 183 having a cross-sectional area gradually decreasing in a downward direction. The liquid sample stored in the concentrated sample storage chamber 380 is sucked by the first pipette 26A functioning as a liquid acquisition section. To realize this, the tip end of the first pipette 26A is configured so as to be lowered to the neighborhood of the tip end of the taper section 183 and the liquid sample is sucked from the neighborhood of the tip end. This configuration allows liquid samples in the concentrated sample storage chamber 380 to be sucked as much as possible and used without waste.

An inclined surface 183a constituting the taper section 183 has the inclination angle θ to the horizontal plane that is not particularly limited in the present invention but is generally in a range from 5 to 45 degrees in consideration of the tip end bore of the first pipette 26A for example. The concentrated sample storage chamber 380 has horizontal cross section and size (cross-sectional area) that can be selected in consideration of the amount of a liquid sample required for the measurement and a predetermined yield.

[Contents of Discrimination/Substitution Processing]

Next, the following section will describe a discrimination/substitution processing using the discrimination/substitution section in the second embodiment. The processing operation by the cell analyzer including the sample preparation apparatus according to the second embodiment is the same as the processing operation of the cell analyzer 1 according to the first embodiment except for the discrimination/substitution processing (Step S10 in the first embodiment). Thus, the same processing operations will not be described further and characteristic discrimination/substitution processings in the second embodiment will be described.

Figure 22:
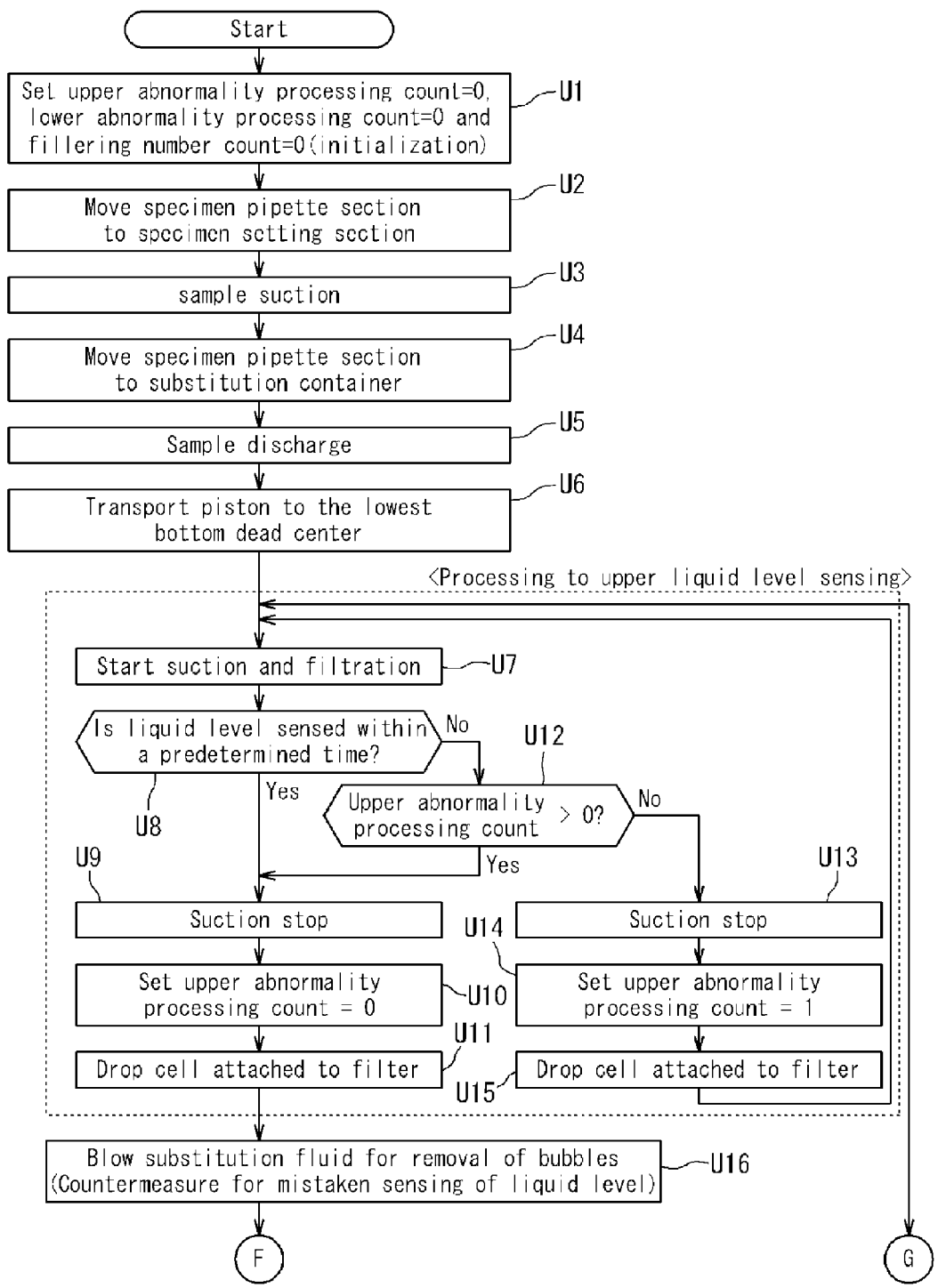
FIG. 22 is a flowchart illustrating a discrimination/substitution processing in a sample preparation apparatus according to another embodiment.
Figure 23:
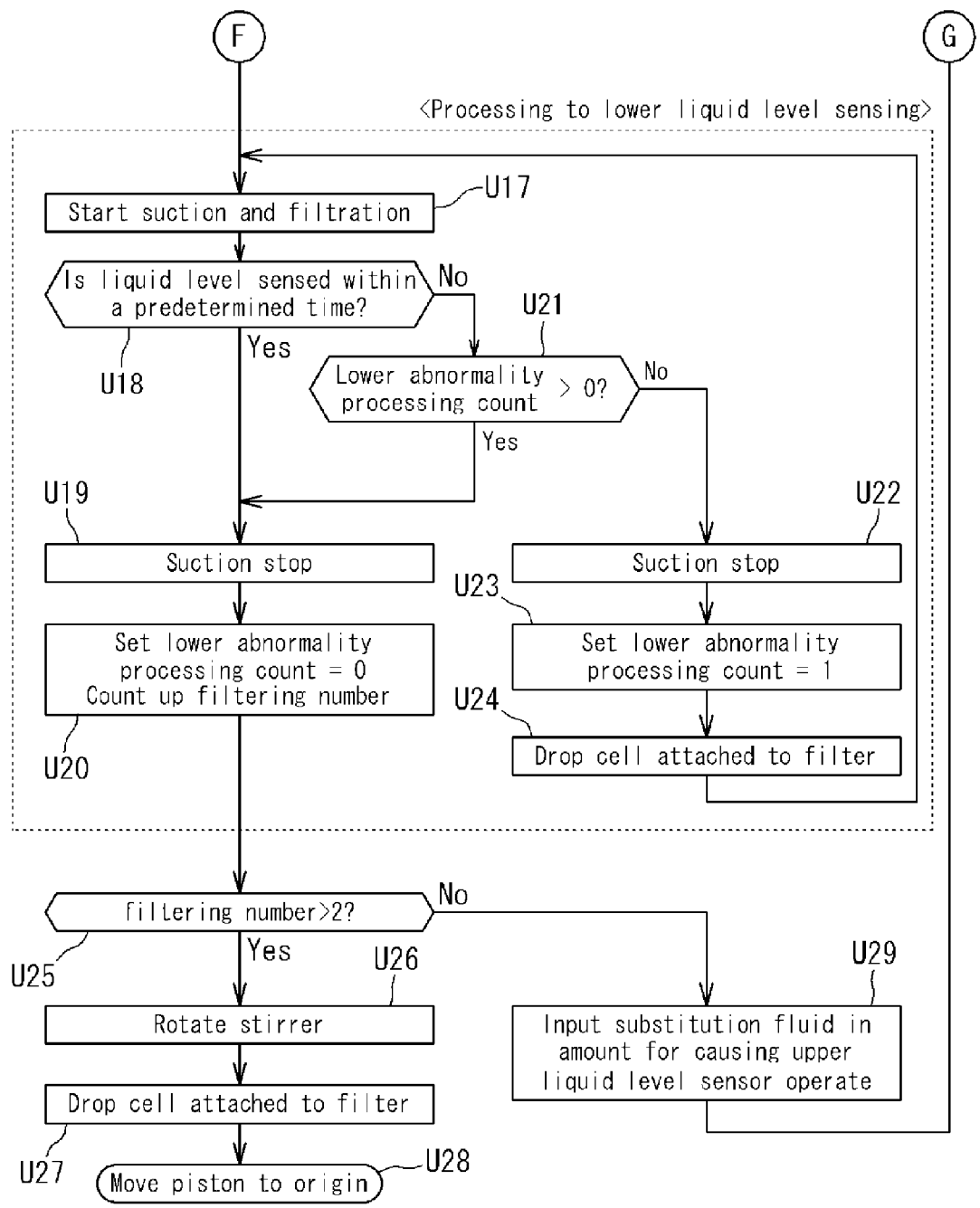
FIG. 23 is a flowchart illustrating a discrimination/substitution processing in a sample preparation apparatus according to another embodiment.

FIG. 22 and FIG. 23 are a flowchart illustrating a discrimination/substitution processing (processings corresponding to Steps T1 to T16 of FIG. 19 to FIG. 20) in the second embodiment.

As shown in FIG. 22, the control section 16 of the sample preparation apparatus firstly performs initialization to set an upper abnormality processing count, a lower abnormality processing count, and a filtering number count to zero (Step U1).

Next, the control section 16 of the sample preparation apparatus causes the specimen pipette section 26 to move to the specimen setting section 24 (Step U2) to thereby cause the first pipette 26A to suck a sample (liquid sample) in the living body container 53 set in the rotation table 24A (Step U3).

Next, the control section 16 causes the specimen pipette section 26 to move to the substitution container 157 (Step U4) to thereby discharge the sample sucked in the first pipette 26A into the substitution container 157 (Step U5).

Next, in Step U6, the piston 158 is transported downwardly to a predetermined lowest bottom dead center.

[Processing to Upper Liquid Level Sensing]

Next, the control section 16 causes the sample in the substitution container 157 to be sucked via the suction tube 200 into the piston 158 (Step U7) for filtration. In parallel with the suction and filtration, the drive motor 170 is driven and the stirrer 172 is rotated via the magnet 169. By rotating the stirrer 172 to thereby agitate the sample in the substitution container 157, the cell as a measurement target can be prevented from being attached to the lower face of the filter 160 by the suction.

Next, the control section 16 determines, in Step U8, whether the upper first liquid level sensor 185 has sensed the liquid level or not when a predetermined time (e.g., 5 seconds) has passed since the start of the suction and filtration. When determining that the first liquid level sensor 185 has sensed the liquid level (Yes), then the processing proceeds to Step U9 to stop the suction by the suction tube 200 and to also stop the rotation of the stirrer 172.

On the other hand, when it is determined in Step U8 that the upper first liquid level sensor 185 has not sensed the liquid level within the predetermined time (No), the control section 16 allows the processing to proceed to Step U12. In Step U12, it is determined whether the upper abnormality processing count is higher than "zero" or not. When the control section 16 determines that the upper abnormality processing count is higher than "zero", then the control section 16 allows the processing to proceed to Step U9 to stop the suction by the suction tube 200 and to also stop the rotation of the stirrer 172. When the control section 16 determines in Step U12 that the upper abnormality processing count is not higher than "zero" (No), then the control section 16 allows the processing to proceed to Step U13 to stop the suction by the suction tube 200 and to also stop the rotation of the stirrer 172.

Next, the control section 16 sets in Step U14 the upper abnormality processing count to "1". In Step U15, a positive pressure is applied to the interior of the piston 158 to drop the cell attached to the lower face of the filter 160 into the sample. Then, the processing returns to Step U7.

In the present embodiment, in order to prevent the decrease of the processing speed due to the cell as a measurement target attached to the lower face of the filter 160, when the upper first liquid level sensor 185 does not sense the liquid level within the predetermined time, it is determined that the cell attached to the lower face of the filter 160 causes the decrease of the speed at which the liquid level declines. Then, in Step U13, the suction and the rotation of the stirrer 172 are stopped. In Step U15, a positive pressure is applied to the interior of the piston 158 to drop the cell attached to the lower face of the filter 160 into the sample.

The suction operation using the upper first liquid level sensor 185 is retried only one time in the present embodiment. In Step U12, when the upper abnormality processing count is higher than "zero" (i.e., the suction operation via Step U13 to Step U15 is retried one time), no further retry is performed and the processing proceeds to Step U9.

The control section 16 causes the suction to be stopped in Step U9 to subsequently set in Step U10 the upper abnormality processing count to "zero".

Next, the control section 16 causes in Step U11 a positive pressure to be applied into the piston 158 as in Step U15 to drop the cell attached to the lower face of the filter 160 into the sample.

Next, the control section 16 causes in Step U16 the substitution fluid blowout tube 190 provided in the vicinity of the upper first liquid level sensor 185 to blow the substitution fluid into the substitution container 157. This processing is for the purpose of removing bubbles generated in the sample in the substitution container 157. The discharge of the sample into the substitution container 157 and the agitation of the sample by the rotation of the stirrer 172 may cause bubbles. The existence of a high amount of such bubbles in the vicinity of the liquid level of the sample causes a declined accuracy at which the liquid level of the sample is detected by the lower second liquid level sensor 182. Specifically, the second liquid level sensor 182 uses the capacitance that is different depending on whether the sensor section 182a has a contact with liquid or has a contact with gas (air). The second liquid level sensor 182 senses, when the change rate of the capacitance is higher than a predetermined value, that the neighborhood of the sensor section 182a changes from liquid to gas or changes from gas to liquid. However, when a high amount of bubbles exist at the liquid level of the sample, an influence by the bubbles causes a reduced change rate of the capacitance. This may consequently cause a case where the liquid level cannot be sensed even when the liquid level has passed the sensor section 182a. A failure to accurately sense the liquid level of the sample makes it impossible to accurately carry out the subsequent processings such as a sample suction.

In the present embodiment, the substitution fluid blowout tube 190 provided in the vicinity of the upper first liquid level sensor 185 is used to blow the substitution fluid into the substitution container 157 to thereby transport the bubbles in the vicinity of the first liquid level sensor 185. When the liquid level of the sample declines to the sensor section 182a of the lower second liquid level sensor 182, bubbles are suppressed from remaining in the vicinity of the sensor section 182a as much as possible. The substitution fluid blowout tube 190 is provided, in the vicinity of the upper first liquid level sensor 185, so that the blowout opening 190a is positioned slightly below the liquid level sensed by the first liquid level sensor 185. Thus, the substitution fluid can be blown to the liquid level to thereby effectively move the bubbles existing in the vicinity of the liquid level. The sensor section 182a of the lower second liquid level sensor 182 is positioned below the upper first liquid level sensor 185. Thus, by moving the bubbles in the vicinity of the sensor section of the upper first liquid level sensor 185, the bubbles remaining in the vicinity of the sensor section 182a of the lower second liquid level sensor 182 can be reduced when the liquid level of the sample declines.

[Processing to Lower Liquid Level Sensing]

Next, in Step U17, the sample in the substitution container 157 is sucked into the piston 158 and is filtered. In parallel with the suction and filtration, the drive motor 170 is driven and the stirrer 172 is rotated via the magnet 169. By rotating the stirrer 172 to agitate the sample in the substitution container 157, it is possible to suppress the attachment of the cell as a measurement target to the lower face of the filter 160 due to the suction.

Next, the control section 16 determines, in Step U18, whether the lower second liquid level sensor 182 has sensed the liquid level when a predetermined time (e.g., 10 seconds) has passed since the start of the suction and filtration or not. When determining that the second liquid level sensor 182 has sensed the liquid level (Yes), the processing proceeds to Step U19 to stop the suction by the suction tube 200 and to also stop the rotation of the stirrer 172.

On the other hand, when determining in Step U18 that the lower second liquid level sensor 182 does not sense the liquid level within the predetermined time (No), the control section 16 allows the processing to proceed to Step U21. In Step U21, it is determined whether the lower abnormality processing count is higher than "zero" or not. When the control section 16 determines that the lower abnormality processing count is higher than "zero", the control section 16 allows the processing to proceed to Step U19 to stop the suction by the suction tube 200 and to also stop the rotation of the stirrer 172. On the other hand, when the control section 16 determines in Step U21 that the lower abnormality processing count is not higher than "zero" (No), the control section 16 allows the processing to proceed to Step U22 to thereby stop the suction by the suction tube 200 and to also stop the rotation of the stirrer 172.

Next, the control section 16 sets in Step U23 the lower abnormality processing count to "1". In Step U24, the control section 16 causes a positive pressure to be applied to the interior of the piston 158 to thereby drop the cell attached to the lower face of the filter 160 into the sample, thereby returning the processing to Step U17.

The suction operation using the lower second liquid level sensor 182 as described above is retried one time in the present embodiment. When it is determined in Step U21 that the lower abnormality processing count is higher than "zero" (i.e., the suction operation via Step U22 to Step U24 is retried one time), no further retry is carried out and the processing returns to Step U19.

Next, the control section 16 stops the suction in Step U19. In Step U20, the control section 16 sets the lower abnormality processing count to "zero" and counts up the filtering number.

Next, the control section 16 determines in Step U25 whether the filtering number is higher than 2 or not. When the control section 16 determines that the filtering number is higher than 2 (Yes) (i.e., when the control section 16 determines that the filtering is performed three times), the control section 16 allows the processing to proceed to Step U26. In Step U26, the control section 16 causes the stirrer 172 to be rotated. Next, in Step U27, a positive pressure is applied to the interior of the piston 158 to thereby drop the cell attached to the lower face of the filter 160 into the sample.

Next, the control section 16 causes in Step U28 the rotation of the stirrer 172 to be stopped to thereby raise the piston 158 lowered to the lowest bottom dead center to an origin.

On the other hand, when the control section 16 determines in Step U25 that the filtering number is not higher than 2 (No), the processing proceeds to Step U29. In Step U29, the substitution fluid in a predetermined amount (e.g., 1 ml) higher than an amount sensed by the upper first liquid level sensor 185 is inputted to the substitution container 157 while rotating the stirrer 172.

When the input of the predetermined amount of the substitution fluid is completed, the control section 16 allows the processing to be returned to Step U7.

In the present embodiment, suction and filtration operations are repeated three times except for the above-described retried suction and filtration.

Other Modified Examples

It is noted that the above disclosed embodiment is an illustration of the present invention and is not the limited one. The scope of the present invention is shown not by the above embodiment but by the claims and includes all modifications equivalent to the configurations in the claims.

For example, a liquid level sensing means for sensing the liquid level in the substitution container 57 may be, in addition to the capacitance-type one, the photoelectric one or the ultrasonic one. In the case of a photoelectric sensor, the sensor can detect the liquid level in the substitution container 57 without protruding a sensor section into the substitution container 57.

Furthermore, although the epidermal cell of a cervix is assumed as a to-be-measured cell in the above embodiment, cancerous determination also can be performed on buccal cells, other epidermal cells such as bladder and pharyngeals as well as epidermal cells of organs.

In the above embodiment, by applying a negative pressure to the interior of the piston 58 and moving the piston 58 downwardly to follow the lowering of the liquid level of the first liquid, the liquid sample is separated into the first liquid and the second liquid. However, another configuration also may be used where the upper opening in the substitution container 57 is configured so that a space between the piston 58 to which the filter 60 is fixed and the substitution container 57 is sealed by a seal member and the piston 58 is downwardly transported by the driving section 59 to thereby separate the liquid sample into the first liquid and the second liquid. Next, the stirrer 72 may be rotated to transport the to-be-measured cell included in the first liquid stored in the storage chamber 68 to the concentrated sample storage chamber 80. Thereafter, the liquid sample existing in the concentrated sample storage chamber 80 may be acquired. This configuration also allows only cells other than an epidermal cell as a to-be-measured cell (e.g., red blood cells and white blood cells) to pass through the filter 60 and prevents the to-be-measured cell of an epidermal cell from passing through the filter 60 to thereby store the to-be-measured cell in the storage chamber 68. Thus, such liquid can be acquired that includes a reduced number of cells other than the to-be-measured cell.

Furthermore, in the above embodiment, a measurement sample prepared by the sample preparation apparatus 3 is measured by a flow cytometer. However, another configuration also may be used that includes: a smear preparation apparatus for smearing a measurement sample prepared by the sample preparation apparatus 3 to a glass slide to prepare a smear sample; and a cell image processing apparatus for imaging the prepared smear sample to analyze an epidermal cell in the imaged image. To the glass slide, there is smeared such a measurement sample that has an epidermal cell as a to-be-measured cell having a higher concentration and that includes a reduced number of cells such as red blood cells and white blood cells. Thus, the epidermal cell can be analyzed accurately.

Furthermore, in the above embodiment, a pressure is applied from the above of the filter 60 to the through hole of the filter 60 after which the stirrer 72 is rotated. However, another order also may be used where the stirrer 72 is rotated after which a pressure is applied from the above of the filter 60 to the through hole of the filter 60. In the above embodiment, the stirrer 72 is rotated while a pressure is being applied to the through hole of the filter 60. However, another configuration also may be used where the stirrer 72 is rotated after the completion of the application of the pressure to the through hole of the filter 60.

Furthermore, in the above embodiment, a to-be-measured cell is selected through the filter 60 provided at the lower end of the piston 58 in the substitution container 57. However, the present invention is not limited to this. Another configuration also may be used where a to-be-measured cell selected by another apparatus is supplied to the substitution container 57.

Furthermore, in the above embodiment (the second embodiment), each number of retry of the suction operation in the processing to upper liquid level sensing and the suction operation in the processing to lower liquid level sensing is set to 1. However, the number of retry may be two or more. Further, although the number of suction and filtration is set to 3, it may be one to two, or may be four or more. These numbers can be selected arbitrarily in consideration of the kind of sample, the concentration of cells as measurement target, the kind of a filter, the processing speed of discrimination/substitution and the like.

Furthermore, in the present embodiment, the bubbles in the sample are suppressed from remaining in the vicinity of the sensor section of the liquid level sensor to influence on liquid level sensing. However, there can be used other method such as addition of antifoaming agent to the sample.

What is claimed is:

1. A sample preparation apparatus, comprising:
    a storage chamber that can store therein a liquid sample including an analysis target to be analyzed;
    a concentrated sample storage chamber that is provided to communicate with the storage chamber and that stores therein concentrated liquid having an analysis target having a higher concentration than that of the liquid sample; and
    a stirrer for transporting the analysis target included in the liquid sample stored in the storage chamber to the concentrated sample storage chamber, wherein the stirrer is provided in the storage chamber,
    a filter for selecting the analysis target to be analyzed, wherein the filter is provided so as to be perpendicular to an axis of rotation of the stirrer, wherein the analysis target to be analyzed selected by the filter is designed to be stored in the storage chamber, and
    a positive pressure blower for peeling an analysis target attached to a face of the filter from the face of the filter, wherein the positive pressure blower is provided so as to locate the filter between the stirrer and the positive pressure blower.

2. The sample preparation apparatus according to claim 1, wherein the stirrer is configured to be rotated by a magnetic force generated by a magnet being configured to be rotated by a drive motor.

3. The sample preparation apparatus according to claim 1, wherein the concentrated sample storage chamber has a smaller cross-sectional area than a cross-sectional area of the storage chamber.

4. The sample preparation apparatus according to claim 1, wherein the concentrated sample storage chamber is provided to communicate with a circumference edge of the storage chamber.

5. The sample preparation apparatus according to claim 1, wherein the concentrated sample storage chamber communicates with the storage chamber via a communication path.

6. The sample preparation apparatus according to claim 5, wherein the storage chamber is composed of a cylindrical body and the communication path is provided along a tangential direction of the cylindrical body.

7. The sample preparation apparatus according to claim 1, further comprising a pipette for acquiring the liquid sample stored in the concentrated sample storage chamber.

8. The sample preparation apparatus according to claim 7, wherein a bottom section of the concentrated sample storage chamber has a taper section having a cross-sectional area gradually decreasing in a downward direction and the liquid acquisition section is configured to acquire the liquid sample from the neighborhood of a tip end of the taper section.

9. The sample preparation apparatus according to claim 1, further comprising a liquid amount sensor for sensing a liquid amount of the liquid sample, in at least one of the storage chamber and the concentrated sample storage chamber.

10. The sample preparation apparatus according to claim 9, wherein the liquid amount sensor comprises a first liquid level sensor for detecting a liquid level of the liquid sample in the storage chamber and a second liquid level sensor for detecting a liquid level of the liquid sample in the concentrated sample storage chamber.

11. The sample preparation apparatus according to claim 10, wherein each tip end of the first liquid level sensor and the second liquid level sensor is provided with a capacitance-type liquid level sensor, and wherein the first liquid level sensor and the second liquid level sensor are so positioned that each tip end thereof is perpendicular or inclined to the liquid level of the liquid sample.

12. The sample preparation apparatus according to claim 1, further comprising a control section comprising a microprocessor, a memory device, a sensor driver and a driving section driver for controlling the positive pressure blower depending on detection of liquid amount by the liquid amount sensor.

13. The sample preparation apparatus according to claim 12, wherein the control section is so configured as to control a number of operation of the positive pressure blower depending on detection of liquid amount by the liquid amount sensor.

14. The sample preparation apparatus according to claim 1, wherein the positive pressure blower is so configured as to apply a positive pressure from an upper face of the filter.

15. The sample preparation apparatus according to claim 1, further comprising a suction tube for transporting non-analysis target included in the liquid sample stored in the storage chamber to the outside of the storage chamber via the filter.

16. The sample preparation apparatus according to claim 15, wherein the suction tube is connected to a negative pressure generator and configured to suck a liquid including the non-analysis target from the storage chamber.

17. The sample preparation apparatus according to claim 16, wherein an open face of a tip end of the suction tube is designed not to be parallel to a filtering face.

18. A cell analyzer comprising:
- a storage chamber that can store therein a liquid sample including an analysis target to be analyzed;
- a concentrated sample storage chamber that is provided to communicate with the storage chamber and that stores therein concentrated liquid sample having an analysis target having a higher concentration than that of the liquid sample;
- a stirrer for transporting the analysis target included in the liquid sample stored in the storage chamber to the concentrated sample storage chamber, wherein the stirrer is provided in the storage chamber;
- a pipette for acquiring the liquid sample including the cell stored in the concentrated sample storage chamber; and
- a data processing apparatus for analyzing a cell included in the liquid sample acquired by the pipette,
- a filter for selecting the analysis target to be analyzed, wherein the filter is provided so as to be perpendicular to an axis of rotation of the stirrer, wherein the analysis target to be analyzed selected by the filter is designed to be stored in the storage chamber, and
- a positive pressure blower for peeling an analysis target attached to a face of the filter from the face of the filter, wherein the positive pressure blower is provided so as to locate the filter between the stirrer and the positive pressure blower.

* * * * *